US010588742B2

(12) United States Patent
Chau et al.

(10) Patent No.: US 10,588,742 B2
(45) Date of Patent: *Mar. 17, 2020

(54) COILED ANCHOR FOR SUPPORTING PROSTHETIC HEART VALVE, PROSTHETIC HEART VALVE, AND DEPLOYMENT DEVICE

(71) Applicant: Mitral Valve Technologies Sarl, Nyon (CH)

(72) Inventors: Mark Chau, Aliso Viejo, CA (US); Alexander J. Siegel, Costa Mesa, CA (US); Paul A. Spence, Louisville, KY (US); Landon H. Tompkins, La Grange, KY (US)

(73) Assignee: Mitral Valve Technologies Sarl, Nyon (CH)

( * ) Notice: Subject to any disclaimer, the term of this patent is extended or adjusted under 35 U.S.C. 154(b) by 207 days.

This patent is subject to a terminal disclaimer.

(21) Appl. No.: 15/912,971

(22) Filed: Mar. 6, 2018

(65) Prior Publication Data

US 2018/0193139 A1 Jul. 12, 2018

Related U.S. Application Data

(60) Division of application No. 14/628,020, filed on Feb. 20, 2015, now Pat. No. 10,052,198, which is a
(Continued)

(51) Int. Cl.
*A61F 2/24* (2006.01)

(52) U.S. Cl.
CPC ............ *A61F 2/2418* (2013.01); *A61F 2/243* (2013.01); *A61F 2210/0014* (2013.01);
(Continued)

(58) Field of Classification Search
CPC .................. A61F 2/2418; A61F 2/243; A61F 2210/0014; A61F 2210/0076; A61F 2230/0091; A61F 2250/0063
See application file for complete search history.

(56) References Cited

U.S. PATENT DOCUMENTS 3,564,617 A 2/1971 Sauvage et al.
3,755,823 A 9/1973 Hancock
(Continued)

FOREIGN PATENT DOCUMENTS

CN 1684644 A 10/2005
CN 1714766 A 1/2006
(Continued)

OTHER PUBLICATIONS

Kempfert et al., "Minimally invasive off-pump valve-in-a-ring implantation: the atrial transcatheter approach for re-operative mitral valve replacement after failed repair," European Journal of Cardiothoracic Surgery, 2009, 35:965-969.
(Continued)

*Primary Examiner* — Phong Son H Dang
(74) *Attorney, Agent, or Firm* — Calfee, Halter & Griswold LLP; Hans P. Smith

(57) ABSTRACT

A system including an anchor for docking a prosthetic valve at a native valve of a heart can have a first end, a second end, and a central axis extending between the first and second ends, and defines an inner space coaxial with the central axis. The valve prosthesis can include a protective layer or annular ring that surrounds a bottom edge of the second frame end. The protective layer or annular ring can include two layers, and the two layers can be different materials.

19 Claims, 25 Drawing Sheets

Related U.S. Application Data continuation-in-part of application No. PCT/US2014/051095, filed on Aug. 14, 2014.

(60) Provisional application No. 61/943,125, filed on Feb. 21, 2014, provisional application No. 61/942,300, filed on Feb. 20, 2014, provisional application No. 61/865,657, filed on Aug. 14, 2013.

(52) U.S. Cl.
CPC ............ *A61F 2210/0076* (2013.01); *A61F 2230/0091* (2013.01); *A61F 2250/0063* (2013.01)

(56) References Cited

U.S. PATENT DOCUMENTS

| | | | |
|---|---|---|---|
| 4,035,849 A | 7/1977 | Angell et al. | |
| 4,490,859 A | 1/1985 | Black et al. | |
| 4,512,338 A | 4/1985 | Balko et al. | |
| 4,759,758 A * | 7/1988 | Gabbay | A61F 2/2412 623/2.13 |
| 4,777,951 A | 10/1988 | Cribier et al. | |
| 4,787,899 A | 11/1988 | Lazarus | |
| 4,796,629 A | 1/1989 | Grayzel | |
| 4,856,516 A | 8/1989 | Hillstead | |
| 4,878,495 A | 11/1989 | Grayzel | |
| 4,966,604 A | 10/1990 | Reiss | |
| 4,994,077 A | 2/1991 | Dobben | |
| 5,059,177 A | 10/1991 | Towne et al. | |
| 5,192,297 A | 3/1993 | Hull | |
| 5,282,847 A | 2/1994 | Trescony et al. | |
| 5,370,685 A | 12/1994 | Stevens | |
| 5,403,305 A | 4/1995 | Sauter et al. | |
| 5,411,552 A | 5/1995 | Andersen et al. | |
| 5,443,500 A | 8/1995 | Sigwart | |
| 5,545,214 A | 8/1996 | Stevens | |
| 5,554,185 A | 9/1996 | Block et al. | |
| 5,558,644 A | 9/1996 | Boyd et al. | |
| 5,584,803 A | 12/1996 | Stevens et al. | |
| 5,591,195 A | 1/1997 | Taheri et al. | |
| 5,607,464 A | 3/1997 | Trescony et al. | |
| 5,665,115 A | 9/1997 | Cragg | |
| 5,769,812 A | 6/1998 | Stevens et al. | |
| 5,800,508 A | 9/1998 | Goicoechea et al. | |
| 5,840,081 A | 11/1998 | Andersen et al. | |
| 5,855,597 A | 1/1999 | Jayaraman | |
| 5,855,601 A * | 1/1999 | Bessler | A61B 17/320725 623/2.38 |
| 5,925,063 A | 7/1999 | Khosravi | |
| 5,957,949 A | 9/1999 | Leonhardt et al. | |
| 6,027,525 A | 2/2000 | Suh et al. | |
| 6,120,534 A | 9/2000 | Ruiz | |
| 6,168,614 B1 | 1/2001 | Andersen et al. | |
| 6,221,091 B1 | 4/2001 | Khosravi | |
| 6,235,042 B1 | 5/2001 | Katzman | |
| 6,245,102 B1 | 6/2001 | Jayaraman | |
| 6,302,906 B1 | 10/2001 | Goicoechea et al. | |
| 6,306,141 B1 | 10/2001 | Jervis | |
| 6,406,492 B1 | 6/2002 | Lytle | |
| 6,409,758 B2 | 6/2002 | Stobie et al. | |
| 6,419,696 B1 | 7/2002 | Ortiz et al. | |
| 6,425,916 B1 | 7/2002 | Garrison et al. | |
| 6,432,134 B1 | 8/2002 | Anson et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,482,228 B1 | 11/2002 | Norred | |
| 6,527,979 B2 | 3/2003 | Constantz | |
| 6,582,462 B1 | 6/2003 | Andersen et al. | |
| 6,625,578 B2 | 9/2003 | Spaur et al. | |
| 6,652,578 B2 | 11/2003 | Bailey et al. | |
| 6,730,118 B2 | 5/2004 | Spenser et al. | |
| 6,730,121 B2 | 5/2004 | Ortiz et al. | |
| 6,733,525 B2 | 5/2004 | Yang et al. | |
| 6,767,362 B2 | 7/2004 | Schreck | |
| 6,797,002 B2 | 9/2004 | Spence et al. | |
| 6,830,584 B1 | 12/2004 | Seguin | |
| 6,878,162 B2 | 4/2005 | Bales et al. | |
| 6,893,460 B2 | 5/2005 | Spenser et al. | |
| 6,908,481 B2 | 6/2005 | Cribier | |
| 6,971,998 B2 | 12/2005 | Rosenman et al. | |
| 7,018,406 B2 | 3/2006 | Seguin et al. | |
| 7,018,408 B2 | 3/2006 | Bailey et al. | |
| 7,037,334 B1 | 5/2006 | Hlavka et al. | |
| 7,077,861 B2 | 7/2006 | Spence | |
| 7,101,395 B2 | 9/2006 | Tremulis et al. | |
| 7,125,421 B2 | 10/2006 | Tremulis et al. | |
| 7,166,126 B2 | 1/2007 | Spence et al. | |
| 7,166,127 B2 | 1/2007 | Spence et al. | |
| 7,276,078 B2 | 10/2007 | Spenser et al. | |
| 7,276,084 B2 | 10/2007 | Yang et al. | |
| 7,318,278 B2 | 1/2008 | Zhang et al. | |
| 7,374,571 B2 | 5/2008 | Pease et al. | |
| 7,393,360 B2 | 7/2008 | Spenser et al. | |
| 7,404,824 B1 | 7/2008 | Webler et al. | |
| 7,431,726 B2 | 10/2008 | Spence et al. | |
| 7,445,632 B2 | 11/2008 | McGuckin, Jr. et al. | |
| 7,462,191 B2 | 12/2008 | Spenser et al. | |
| 7,510,575 B2 | 3/2009 | Spenser et al. | |
| 7,527,646 B2 | 5/2009 | Rahdert et al. | |
| 7,585,321 B2 | 9/2009 | Cribier | |
| 7,618,446 B2 | 11/2009 | Andersen et al. | |
| 7,618,449 B2 | 11/2009 | Tremulis et al. | |
| 7,655,034 B2 | 2/2010 | Mitchell et al. | |
| 7,737,060 B2 | 6/2010 | Strickler et al. | |
| 7,758,639 B2 | 7/2010 | Mathis | |
| 7,780,726 B2 | 8/2010 | Seguin | |
| 7,785,366 B2 | 8/2010 | Maurer et al. | |
| 7,942,927 B2 | 5/2011 | Kaye et al. | |
| 7,951,195 B2 | 5/2011 | Antonsson et al. | |
| 7,955,385 B2 | 6/2011 | Crittenden | |
| 7,959,672 B2 | 6/2011 | Salahieh et al. | |
| 7,993,394 B2 | 8/2011 | Hariton et al. | |
| 8,016,882 B2 | 9/2011 | Macoviak et al. | |
| 8,029,556 B2 | 10/2011 | Rowe | |
| 8,052,750 B2 | 11/2011 | Tuval et al. | |
| 8,092,520 B2 | 1/2012 | Quadri | |
| 8,128,691 B2 | 3/2012 | Keranen | |
| 8,167,932 B2 | 5/2012 | Bourang et al. | |
| 8,236,049 B2 | 8/2012 | Rowe et al. | |
| 8,323,335 B2 | 12/2012 | Rowe et al. | |
| 8,377,115 B2 | 2/2013 | Thompson | |
| 8,398,708 B2 | 3/2013 | Meiri et al. | |
| 8,449,605 B2 | 5/2013 | Lichtenstein et al. | |
| 8,449,606 B2 | 5/2013 | Eliasen et al. | |
| 8,652,203 B2 | 2/2014 | Quadri et al. | |
| 8,657,872 B2 | 2/2014 | Seguin | |
| 8,663,322 B2 | 3/2014 | Keranen | |
| 8,672,998 B2 | 3/2014 | Lichtenstein et al. | |
| 8,734,507 B2 | 5/2014 | Keranen | |
| 8,795,352 B2 | 8/2014 | O'Beirne et al. | |
| 8,986,373 B2 | 3/2015 | Chau et al. | |
| 9,078,747 B2 | 7/2015 | Conklin | |
| 9,095,434 B2 | 8/2015 | Rowe | |
| 9,119,718 B2 | 9/2015 | Keranen | |
| 9,180,006 B2 * | 11/2015 | Keranen | A61F 2/2448 |
| 9,237,886 B2 | 1/2016 | Seguin et al. | |
| 9,364,326 B2 | 6/2016 | Yaron | |
| 9,463,268 B2 | 10/2016 | Spence | |
| 9,474,599 B2 | 10/2016 | Keranen | |
| 9,622,863 B2 | 4/2017 | Karapetian et al. | |
| 9,700,409 B2 * | 7/2017 | Braido | A61F 2/2418 |
| 2002/0026094 A1 | 2/2002 | Roth | |
| 2002/0032481 A1 | 3/2002 | Gabbay | |
| 2002/0045936 A1 | 4/2002 | Moe | |
| 2002/0055773 A1 * | 5/2002 | Campbell | A61F 2/2409 623/2.4 |
| 2002/0138135 A1 | 9/2002 | Duerig et al. | |
| 2002/0173841 A1 | 11/2002 | Ortiz et al. | |
| 2003/0050694 A1 | 3/2003 | Yang et al. | |
| 2003/0100939 A1 | 5/2003 | Yodfat et al. | |
| 2003/0158597 A1 | 8/2003 | Quiachon et al. | |
| 2003/0167089 A1 | 9/2003 | Lane | |

(56) References Cited

U.S. PATENT DOCUMENTS

| | | |
|---|---|---|
| 2003/0212454 A1 | 11/2003 | Scott et al. |
| 2003/0225420 A1 | 12/2003 | Wardle |
| 2004/0167620 A1 | 8/2004 | Ortiz et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0096736 A1 | 5/2005 | Osse et al. |
| 2005/0119735 A1 | 6/2005 | Spence et al. |
| 2005/0137691 A1 | 6/2005 | Salahieh et al. |
| 2005/0149178 A1* | 7/2005 | Spence .............. A61F 2/2445 623/2.11 |
| 2005/0182486 A1 | 8/2005 | Gabbay |
| 2005/0203614 A1 | 9/2005 | Forster et al. |
| 2005/0203617 A1 | 9/2005 | Forster et al. |
| 2005/0228496 A1* | 10/2005 | Mensah ............... A61F 2/2409 623/2.41 |
| 2005/0234546 A1 | 10/2005 | Nugent et al. |
| 2006/0025857 A1 | 2/2006 | Bergheim et al. |
| 2006/0052867 A1* | 3/2006 | Revuelta .............. A61F 2/2418 623/2.18 |
| 2006/0058872 A1 | 3/2006 | Salahieh et al. |
| 2006/0149350 A1 | 7/2006 | Patel et al. |
| 2006/0195185 A1 | 8/2006 | Lane et al. |
| 2006/0265056 A1 | 11/2006 | Nguyen et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0185572 A1 | 8/2007 | Solem et al. |
| 2007/0203503 A1 | 8/2007 | Salahieh et al. |
| 2007/0203575 A1 | 8/2007 | Forster et al. |
| 2007/0213813 A1 | 9/2007 | Von Segesser et al. |
| 2007/0232898 A1 | 10/2007 | Huynh et al. |
| 2007/0244553 A1 | 10/2007 | Rafiee et al. |
| 2007/0265700 A1 | 11/2007 | Eliasen et al. |
| 2008/0004697 A1 | 1/2008 | Lichtenstein et al. |
| 2008/0021547 A1* | 1/2008 | Davidson ............. A61F 2/2409 623/2.41 |
| 2008/0033542 A1 | 2/2008 | Antonsson et al. |
| 2008/0114442 A1 | 5/2008 | Mitchell et al. |
| 2008/0125853 A1 | 5/2008 | Bailey et al. |
| 2008/0200977 A1* | 8/2008 | Paul ..................... A61F 2/2412 623/1.24 |
| 2008/0208330 A1 | 8/2008 | Keranen |
| 2008/0228265 A1 | 9/2008 | Spence et al. |
| 2008/0243245 A1 | 10/2008 | Thambar et al. |
| 2008/0275503 A1 | 11/2008 | Spence et al. |
| 2009/0005863 A1 | 1/2009 | Goetz et al. |
| 2009/0157175 A1 | 6/2009 | Benichou |
| 2009/0177278 A1 | 7/2009 | Spence |
| 2009/0234318 A1 | 9/2009 | Loulmet et al. |
| 2009/0259307 A1 | 10/2009 | Gross et al. |
| 2009/0276038 A1 | 11/2009 | Tremulis et al. |
| 2009/0276040 A1 | 11/2009 | Rowe et al. |
| 2009/0281619 A1 | 11/2009 | Le et al. |
| 2009/0299471 A1 | 12/2009 | Keranen |
| 2009/0319037 A1 | 12/2009 | Rowe et al. |
| 2010/0049313 A1 | 2/2010 | Alon et al. |
| 2010/0076548 A1* | 3/2010 | Konno ................ A61F 2/2412 623/2.1 |
| 2010/0076549 A1 | 3/2010 | Keidar et al. |
| 2010/0145440 A1 | 6/2010 | Keranen |
| 2010/0152839 A1 | 6/2010 | Shandas et al. |
| 2010/0161047 A1 | 6/2010 | Cabiri |
| 2010/0168844 A1 | 7/2010 | Toomes et al. |
| 2010/0198347 A1 | 8/2010 | Zakay et al. |
| 2010/0217382 A1 | 8/2010 | Chau et al. |
| 2010/0217385 A1 | 8/2010 | Thompson et al. |
| 2010/0312333 A1 | 12/2010 | Navia et al. |
| 2010/0318183 A1 | 12/2010 | Keranen |
| 2010/0318184 A1 | 12/2010 | Spence |
| 2010/0331971 A1 | 12/2010 | Keranen et al. |
| 2010/0331973 A1 | 12/2010 | Keranen |
| 2011/0015729 A1 | 1/2011 | Jimenez et al. |
| 2011/0098802 A1 | 4/2011 | Braido et al. |
| 2011/0106247 A1 | 5/2011 | Miller et al. |
| 2011/0137397 A1 | 6/2011 | Chau et al. |
| 2011/0178597 A9 | 7/2011 | Navia et al. |
| 2011/0196480 A1 | 8/2011 | Cartledge |
| 2011/0208297 A1 | 8/2011 | Tuval et al. |
| 2011/0208298 A1 | 8/2011 | Tuval et al. |
| 2011/0218621 A1 | 9/2011 | Antonsson et al. |
| 2011/0224785 A1 | 9/2011 | Hacohen |
| 2011/0245911 A1 | 10/2011 | Quill et al. |
| 2011/0288634 A1 | 11/2011 | Tuval et al. |
| 2011/0295361 A1 | 12/2011 | Claiborne, III et al. |
| 2011/0319989 A1 | 12/2011 | Lane et al. |
| 2011/0319990 A1 | 12/2011 | Macoviak et al. |
| 2012/0016464 A1 | 1/2012 | Seguin |
| 2012/0022633 A1 | 1/2012 | Olson et al. |
| 2012/0053680 A1 | 3/2012 | Bolling et al. |
| 2012/0059458 A1 | 3/2012 | Buchbinder et al. |
| 2012/0123529 A1 | 5/2012 | Levi et al. |
| 2012/0150287 A1 | 6/2012 | Forster et al. |
| 2012/0259409 A1 | 10/2012 | Nguyen et al. |
| 2012/0283820 A1 | 11/2012 | Tseng et al. |
| 2012/0310328 A1 | 12/2012 | Olson et al. |
| 2012/0316643 A1 | 12/2012 | Keranen |
| 2012/0323316 A1* | 12/2012 | Chau ................... A61F 2/2418 623/2.18 |
| 2013/0006352 A1 | 1/2013 | Yaron |
| 2013/0023985 A1 | 1/2013 | Khairkhahan et al. |
| 2013/0114214 A1 | 5/2013 | Takeguchi et al. |
| 2013/0190857 A1 | 7/2013 | Mitra et al. |
| 2013/0274873 A1 | 10/2013 | Delaloye et al. |
| 2013/0310917 A1 | 11/2013 | Richter et al. |
| 2013/0310928 A1 | 11/2013 | Morriss et al. |
| 2013/0317598 A1 | 11/2013 | Rowe et al. |
| 2013/0325114 A1 | 12/2013 | McLean et al. |
| 2013/0331929 A1 | 12/2013 | Mitra et al. |
| 2014/0074299 A1 | 3/2014 | Endou et al. |
| 2014/0155997 A1* | 6/2014 | Braido ................ A61F 2/2433 623/2.37 |
| 2014/0172070 A1 | 6/2014 | Seguin |
| 2014/0194981 A1 | 7/2014 | Menk et al. |
| 2014/0200661 A1 | 7/2014 | Pintor et al. |
| 2014/0236287 A1 | 8/2014 | Clague et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0330372 A1 | 11/2014 | Weston et al. |
| 2014/0343671 A1 | 11/2014 | Yohanan et al. |
| 2014/0350667 A1 | 11/2014 | Braido et al. |
| 2014/0358224 A1* | 12/2014 | Tegels ................. A61L 27/14 623/2.14 |
| 2014/0379074 A1 | 12/2014 | Spence et al. |
| 2014/0379076 A1* | 12/2014 | Vidlund .............. A61F 2/2418 623/2.18 |
| 2015/0073545 A1 | 3/2015 | Braido |
| 2015/0073546 A1 | 3/2015 | Braido |
| 2015/0230921 A1 | 8/2015 | Chau et al. |
| 2015/0282931 A1 | 10/2015 | Brunnett et al. |
| 2015/0335428 A1 | 11/2015 | Keranen |
| 2015/0374493 A1 | 12/2015 | Yaron et al. |
| 2016/0074165 A1 | 3/2016 | Spence et al. |
| 2016/0095705 A1 | 4/2016 | Keranen et al. |
| 2016/0184095 A1 | 6/2016 | Spence et al. |
| 2016/0199177 A1 | 7/2016 | Spence et al. |
| 2016/0256276 A1 | 9/2016 | Yaron |
| 2017/0007399 A1 | 1/2017 | Keranen |
| 2017/0007402 A1 | 1/2017 | Zerkowski et al. |

FOREIGN PATENT DOCUMENTS

| | | |
|---|---|---|
| CN | 101588771 A | 11/2009 |
| DE | 19532846 A1 | 3/1997 |
| DE | 19546692 A1 | 6/1997 |
| DE | 19857887 A1 | 7/2000 |
| DE | 19907646 A1 | 8/2000 |
| EP | 0103546 A1 | 3/1984 |
| EP | 0592410 A1 | 4/1994 |
| EP | 0597967 A1 | 5/1994 |

(56) References Cited

FOREIGN PATENT DOCUMENTS

| | | |
|---|---|---|
| EP | 0850607 A1 | 7/1998 |
| EP | 1432369 A1 | 6/2004 |
| EP | 1521550 A2 | 4/2005 |
| EP | 1796597 A2 | 6/2007 |
| EP | 1827314 A1 | 9/2007 |
| EP | 1296618 B1 | 1/2008 |
| EP | 2072027 A1 | 6/2009 |
| EP | 1827314 B1 | 12/2010 |
| EP | 2620125 A1 | 7/2013 |
| EP | 2726018 A2 | 5/2014 |
| EP | 2806829 A2 | 12/2014 |
| FR | 2788217 A1 | 7/2000 |
| FR | 2815844 A1 | 5/2002 |
| SU | 1271508 A1 | 11/1986 |
| WO | 9117720 A1 | 11/1991 |
| WO | 9301768 A1 | 2/1993 |
| WO | 9829057 A1 | 7/1998 |
| WO | 9940964 A1 | 8/1999 |
| WO | 9947075 A1 | 9/1999 |
| WO | 0041652 A1 | 7/2000 |
| WO | 0047139 A1 | 8/2000 |
| WO | 0149213 A2 | 7/2001 |
| WO | 0154625 A1 | 8/2001 |
| WO | 0162189 A1 | 8/2001 |
| WO | 0164137 A1 | 9/2001 |
| WO | 0176510 A2 | 10/2001 |
| WO | 0203892 A1 | 1/2002 |
| WO | 0222054 A1 | 3/2002 |
| WO | 0236048 A1 | 5/2002 |
| WO | 0247575 A2 | 6/2002 |
| WO | 03047468 A1 | 6/2003 |
| WO | 05/034812 | 4/2005 |
| WO | 2005084595 A1 | 9/2005 |
| WO | 2005102015 A2 | 11/2005 |
| WO | 2006011127 A2 | 2/2006 |
| WO | 2006091163 A1 | 8/2006 |
| WO | 2006111391 A1 | 10/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008058940 A1 | 5/2008 |
| WO | 2008091515 A2 | 7/2008 |
| WO | 2009033469 A1 | 3/2009 |
| WO | 2009134701 A2 | 11/2009 |
| WO | 2010057262 A1 | 5/2010 |
| WO | 2010121076 A2 | 10/2010 |
| WO | 2013001339 A2 | 1/2013 |
| WO | 2013068542 A1 | 5/2013 |
| WO | 2013110722 A2 | 8/2013 |
| WO | 2013114214 A2 | 8/2013 |
| WO | 2015023579 A1 | 2/2015 |
| WO | 2015023862 A2 | 2/2015 |
| WO | 2015127264 A1 | 8/2015 |
| WO | 2015198125 A1 | 12/2015 |
| WO | 2016038017 A1 | 3/2016 |
| WO | 2016040881 A1 | 3/2016 |
| WO | 2016130820 A1 | 8/2016 |

OTHER PUBLICATIONS

Webb et al., "Transcatheter Valve-in-Valve Implantation for Failed Bioprosthetic Heart Valves," Journal of the American Heart Association, 11, Apr. 27, 2010.

Webb et al., "Mitral Valve in Valve," TCT Sep. 2009, Live Case: 30 Minutes, St. Paul's Hospital/University of British Columbia.

Wenaweser et al., "Percutaneous Aortic Valve Replacement for Severe Aortic Regurgitation in Degenerated Bioprosthesis: The First Valve Procedure Using Corevalve Revalving System," Catheterization and Cardiovascular Interventions, 70:760-764, 2007.

Cheung et al., "Transapical Transcatheter Mitral Valve-in-Valve Implantation in a Human," The Society of Thoracic Surgeons, 2009.

Cheung et al, Live Case Transmissions, NYHA III CHF, Case Summary, Sep. 23, 2010, St. Paul's Hospital/University of British Columbia.

Shuto et al., "Percutaneous Transvenous Melody Valve-in-Ring Procedure for Mitral Valve Replacement," J Am Coll Cardiol, 58(24): 2475-2480, 2011.

Descoutures et al., "Transcatheter Valve-in-Ring Implantation After Failure of Surgical Mitral Repair," European Journal of Cardio-Thoracic Surgery 44, e8-e15, 2013.

Weger et al., "First-in-Man Implantation of a Trans-Catheter Aortic Valve in a Mitral Annuloplasty Ring: Novel Treatment Modality for Failed Mitral Valve Repair," European Journal of Cardio-Thoracic Surgery 39, 1054-1056, 2011.

Walther et al., "Human Minimally Invasive Off-Pump Valve-in-a-Valve Implantation," Case Reports, The Society of Thoracic Surgeons, 2008.

Walther et al., "Valve-in-a-Valve Concept for Transcatheter Minimally Invasive Repeat Xenograph Implantation," Preclinical Studies, Journal of the American College of Cardiology, 2007.

Himbert et al., "Transseptal Implantation of a Transcatheter Heart Valve in a Mitral Annuloplasty Ring to Treat Mitral Repair Failure," Circulation Cardiovascular Interventions, American Heart Association, 2011.

Himbert, Dominique, "Transvenous Mitral Valve Repair Replacement After Failure of Surgical Ring Annuloplasty," Research Correspondence, Journal of the American College of Cardiology, 2012.

Casselman et al., "Reducing Operative Morality in Valvular Reoperations: The "valve in ring" Procedure," Brief Technique Reports, The Journal of Thoracic and Cardiovascular Surgery, vol. 141, No. 5. May 2011.

Ma et al., "Double-Crowned Valved Stents for Off-Pump Mitral Valve Replacement," European Journal of Cardio-Thoracic Surgery, 28, 194-199, 2005.

Bonhoeffer et at., "Percutaneous Replacement of Pulmonary valve in a Right-Ventricle to Pulmonary-Artery Prosthetic Conduit with Valve Dysfunction," Early Report, The Lancet, vol. 356, Oct. 21, 2000.

International Search Report from corresponding PCT case No. PCT/IB2015/000901 dated Feb. 15, 2015.

Andersen, H.R., et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.

Andersen, H.R. "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

\* cited by examiner

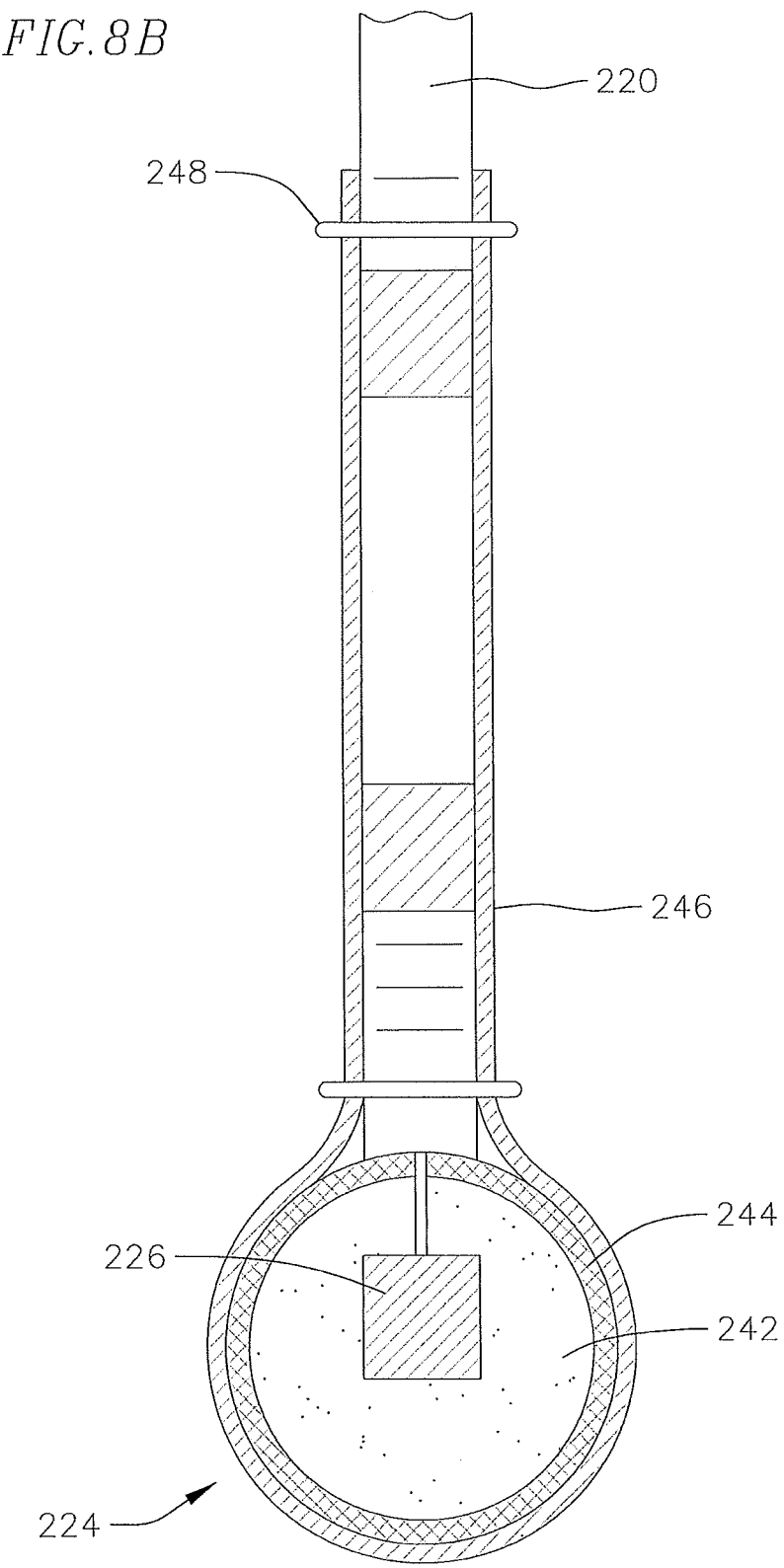

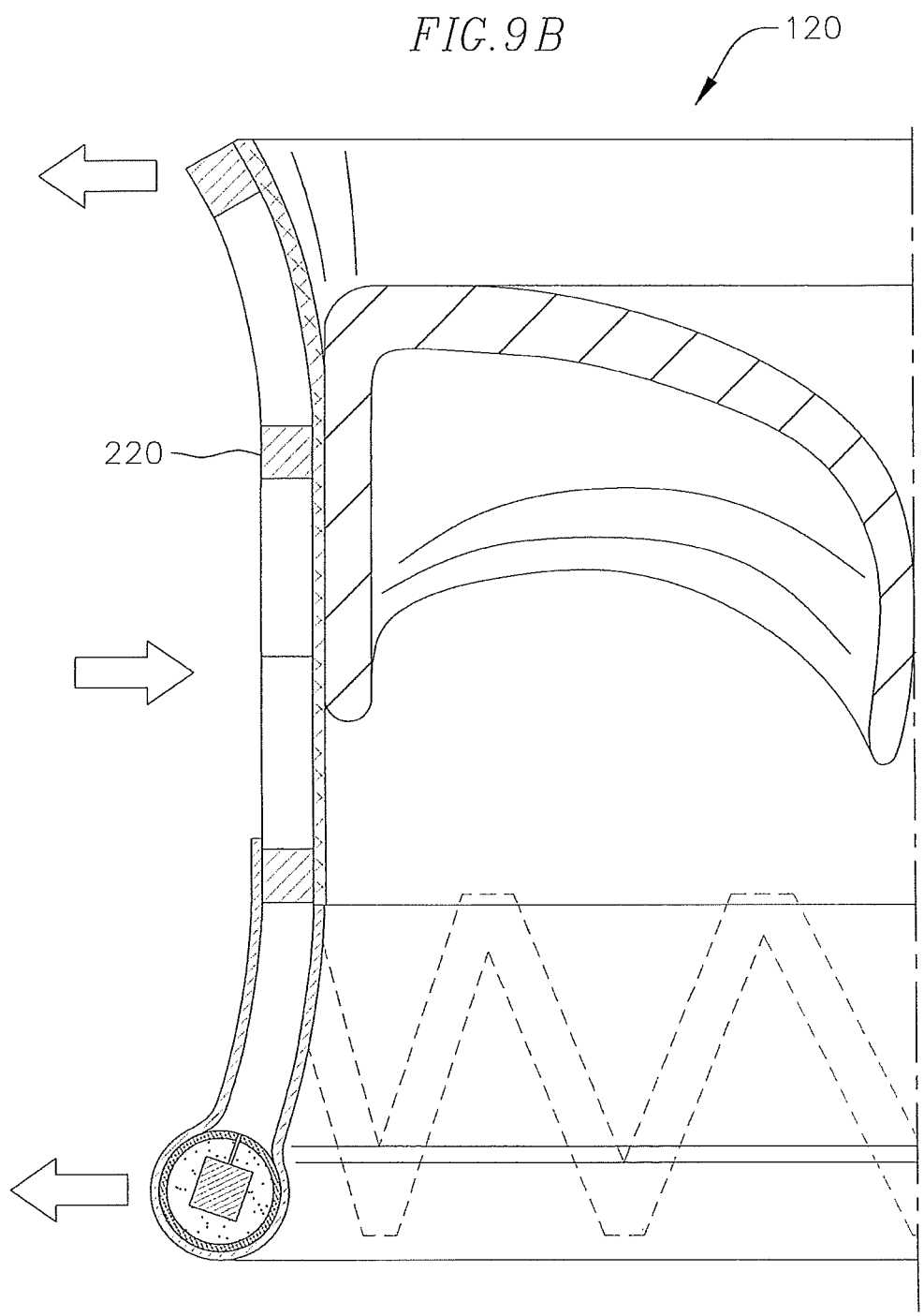

COILED ANCHOR FOR SUPPORTING PROSTHETIC HEART VALVE, PROSTHETIC HEART VALVE, AND DEPLOYMENT DEVICE

CROSS-REFERENCE TO RELATED APPLICATION(S)

The present application is a continuation of U.S. patent application Ser. No. 14/628,020, filed Feb. 20, 2015, which is a continuation-in-part of International Application PCT/US2014/051095, with an international filing date of Aug. 14, 2014, which claims the benefit of U.S. Provisional Applications No. 61/865,657 filed Aug. 14, 2013, No. 61/942,300 filed Feb. 20, 2014, and No. 61/943,125 filed Feb. 21, 2014

BACKGROUND FIELD

The invention generally relates to medical devices and procedures pertaining to prosthetic heart valves. More specifically, the invention relates to replacement of heart valves that may have malformations and/or dysfunctions. Embodiments of the invention relate to a prosthetic heart valve for replacing a mitral valve in the heart, an anchor to facilitate and maintain a positioning of the prosthetic heart valve in the native valve, and deployment devices and procedures associated with implantation of the prosthetic heart valve.

DESCRIPTION OF RELATED ART

Referring first generally to FIGS. 1 and 2, the mitral valve controls the flow of blood between the left atrium and the left ventricle of the human heart. After the left atrium receives oxygenated blood from the lungs via the pulmonary veins, the mitral valve permits the flow of the oxygenated blood from the left atrium into the left ventricle. When the left ventricle contracts, the oxygenated blood held in the left ventricle is delivered through the aortic valve and the aorta to the rest of the body. Meanwhile, the mitral valve closes during ventricular contraction, to prevent the flow of blood back into the left atrium.

When the left ventricle contracts, the blood pressure in the left ventricle increases substantially, and urges the mitral valve closed. Due to the large pressure differential between the left ventricle and the left atrium during ventricular contraction, a possibility of prolapse, or eversion of the leaflets of the mitral valve back into the atrium, arises. To prevent this, a series of chordae tendineae connect the mitral valve to the papillary muscles along opposing walls of the left ventricle. The chordae tendineae are schematically illustrated in both the heart cross-section of FIG. 1 and the top view of the mitral valve in FIG. 2. Just before and during ventricular contraction, the papillary muscles also contract and maintain tension in the chordae tendineae, to hold the leaflets of the mitral valve in the closed position and preventing them from turning inside-out and back into the atrium, thereby also preventing backflow of the oxygenated blood into the atrium.

A general shape of the mitral valve and its leaflets as seen from the left atrium is illustrated in FIG. 2. Complications of the mitral valve can potentially cause fatal heart failure. One form of valvular heart disease is mitral valve leak, also known as mitral regurgitation, characterized by the abnormal leaking of blood from the left ventricle back into the left atrium through the mitral valve. In these circumstances, it may be desirable to repair the mitral valve or to replace the functionality of the mitral valve with that of a prosthetic heart valve.

To this point, mitral valve repair has been more popular than valve replacement, where prior research and development has been limited. There are little or no effective commercially available ways to replace a mitral valve through catheter implantation and/or other minimal or less invasive procedures. In contrast, the field of transcatheter aortic valve replacement has developed and has gained widespread success. This discrepancy stems from replacement of a mitral valve being more difficult than aortic valve replacement in many respects, for example, due to the physical structure of the valve and more difficult access to the valve.

The most prominent obstacle for mitral valve replacement is anchoring or retaining the valve in position, due to the valve being subject to a large cyclic load. Especially during ventricular contraction, the movement of the heart and the load on the valve may combine to shift or dislodge a prosthetic valve. Also, the movement and rhythmic load can fatigue materials, leading to fractures of the implanted valve. If the orientation of a mitral prosthesis is unintentionally shifted, blood flow between the left atrium and the left ventricle may be obstructed or otherwise negatively affected. While puncturing the tissue in or around the mitral valve annulus to better anchor an implanted valve is an option for retaining the placement of the implant, this may potentially lead to unintended perforation of the heart and patient injury.

Referring back to FIG. 2, another issue with mitral valve replacement is the size and shape of the native mitral valve. Aortic valves are more circular in shape than mitral valves. Furthermore, in many cases, the need for aortic valve replacement arises due to, for example, aortic valve stenosis, when the aortic valve narrows due to reasons such as calcification and/or hardening of the aortic valve leaflets. As such, the aortic valve annulus itself generally forms a more stable anchoring site for a prosthetic valve than a mitral valve annulus, which is quite large and non-circular. As such, a circular mitral valve implant that is too small may cause leaks around the implanted valve (i.e., paravalvular leak) if a good seal is not established around the valve. Meanwhile, a circular valve implant that is too large may stretch out and damage the valve annulus. The outer shape of a valve implant can also potentially be manipulated to better fit the mitral valve annulus, for example, through fabric cuff additions on an outer surface of the implant. However, these additions may restrict valve delivery through a catheter and/or minimally invasive procedures, since the additional fabric may be difficult to compress and deploy through a catheter.

SUMMARY

Since many valves have been developed for the aortic position, it would be desirable to try to take advantage of these existing valve technologies and to utilize the same or similar valves in mitral valve replacements. It would therefore be useful to create a mitral anchor or docking station for such preexisting prosthetic valves. An existing valve developed for the aortic position, perhaps with some modification, could then be implanted in such an anchor or docking station. Some previously developed valves may fit well with little or no modification, such as the Edwards Lifesciences Sapien™ valve.

It would therefore be desirable to provide devices and methods that can be utilized in a variety of implantation approaches to facilitate the docking or anchoring of such valves. Embodiments of the invention provide a stable docking station for retaining a mitral valve replacement prosthesis. Other devices and methods are provided to improve the positioning and deployment of such docking stations and/or the replacement prosthesis therein, for example, during various non-invasive or minimally invasive procedures. The devices and methods may also serve to prevent or greatly reduce regurgitation or leaking of blood around the replacement prosthesis, such as leakage through the commissures of the native mitral valve outside of the prosthesis.

Features of the invention are directed to a docking or anchoring device that more effectively anchors a replacement valve prosthesis in the mitral valve annulus. Other features of the invention are directed to a replacement valve prosthesis that more effectively interacts with an anchoring device according to embodiments of the invention and with surrounding portions of the native mitral valve and other portions of the heart. Still other features of the invention are directed to docking or anchoring devices and methods for more effectively deploying different portions of the anchoring devices above and below the native mitral valve annulus (i.e., deploying separate portions of the anchoring devices into the left atrium and left ventricle, respectively). Still other features of the invention are directed to corralling or holding the chordae tendineae together during deployment of the docking or anchoring devices, to more easily position the docking or anchoring devices around the native valve leaflets and the chordae tendineae.

In an embodiment of the invention, a coiled anchor for docking a mitral valve prosthesis at a native mitral valve of a heart has a first end, a second end, and a central axis extending between the first and second ends, and defines an inner space coaxial with the central axis. The coiled anchor includes a coiled core including a bio-compatible metal or metal alloy and having a plurality of turns extending around the central axis in a first position, and a cover layer around the core, the cover layer including a bio-compatible material that is less rigid than the metal or metal alloy of the coiled core. The coiled anchor is adjustable from the first position to a second position wherein at least one of the plurality of turns is straightened for the coiled anchor to be delivered through a catheter to the native mitral valve, and from the second position back to the first position. The coiled anchor is implantable at the native mitral valve with at least a portion on one side of the native mitral valve in a left atrium of the heart and at least a portion on an opposite side of the native mitral valve in a left ventricle of the heart, to support or hold the mitral valve prosthesis in the inner space when the coiled anchor is implanted at the native mitral valve.

In another embodiment, the coiled anchor can be included in a system for implanting at a mitral valve, where the system can further include a mitral valve prosthesis including an expandable frame and housing a plurality of leaflets for controlling blood flow therethrough, wherein the frame is expandable from a collapsed first position wherein the frame has a first outer diameter for delivery of the mitral valve prosthesis through a catheter to an expanded second position wherein the frame has a second outer diameter greater than the first outer diameter. When the coiled anchor and the mitral valve prosthesis are unbiased, a smallest inner diameter of the inner space defined by the coil anchor can be smaller than the second outer diameter of the mitral valve prosthesis.

In another embodiment, a coiled anchor for docking a mitral valve prosthesis at a native mitral valve of a heart has a first end, a second end, and a central axis extending between the first and second ends, and defines an inner space coaxial with the central axis. The coiled anchor includes a first coil having a plurality of turns in a first circumferential direction and extending from a first end to a second end, a second coil having a plurality of turns in a second circumferential direction opposite to the first circumferential direction and extending from a first end to a second end, and a joint configured to hold the first end of the first coil and the first end of the second coil together, such that the first and second coils each extends away from the joint and from one another along the central axis. The coiled anchor has a first position where the respective turns of the first coil and the second coil each extends around the central axis. The coiled anchor is adjustable from the first position to a second position wherein at least one of the plurality of turns of the first coil or the second coil is straightened for the coiled anchor to be delivered through a catheter to the native mitral valve, and from the second position back to the first position. The coiled anchor is implantable at the native mitral valve with at least a portion of the first coil on one side of the native mitral valve in a left atrium of the heart, and at least a portion of the second coil on an opposite side of the native mitral valve in a left ventricle of the heart, to support or hold the mitral valve prosthesis in the inner space when the coiled anchor is implanted at the native mitral valve.

In another embodiment, a method for delivering a coiled anchor that is configured to dock a mitral valve prosthesis at a native mitral valve of a heart includes positioning a catheter for delivery of the coiled anchor at the native mitral valve, positioning a loop around chordae tendineae, closing the loop to draw the chordae tendineae together, advancing the coiled anchor out of the catheter and around the chordae tendineae, and removing the loop and the catheter.

According to embodiments of the invention, mitral valve replacement can be realized through a variety of different implantation approaches. Embodiments of the invention thus provide flexibility with different ways and options for implanting a replacement mitral valve.

BRIEF DESCRIPTION OF THE DRAWINGS

Further features and advantages of the invention will become apparent from the description of embodiments using the accompanying drawings. In the drawings:

FIGS. 8A and 8B respectively show a perspective schematic view of an exemplary transcatheter valve prosthesis, and a cross-section of a portion of the valve prosthesis, according to an embodiment of the invention;

FIGS. 9A and 9B respectively show a valve prosthesis held in a helical coil according to an embodiment of the invention, and a flaring that occurs to a frame of the valve prosthesis according to an embodiment of the invention;

DETAILED DESCRIPTION

Figure 3A:
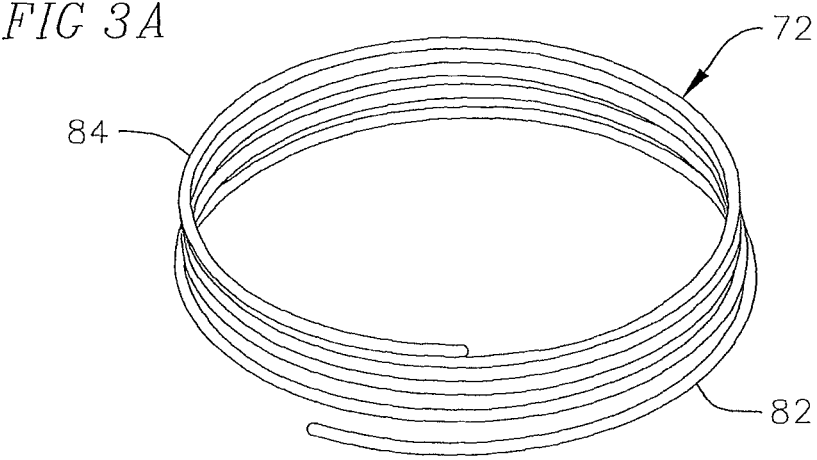
FIGS. 3A to 3E show various views of a coil anchor according to an embodiment of the invention.
Figure 3B:
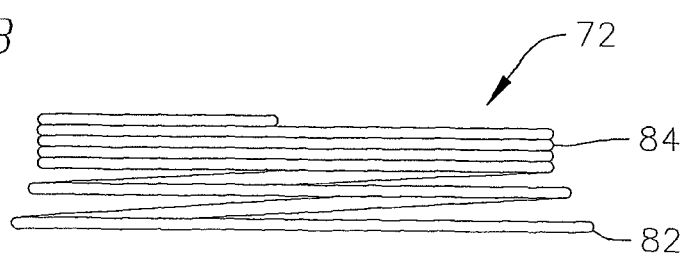
Figure 3C:
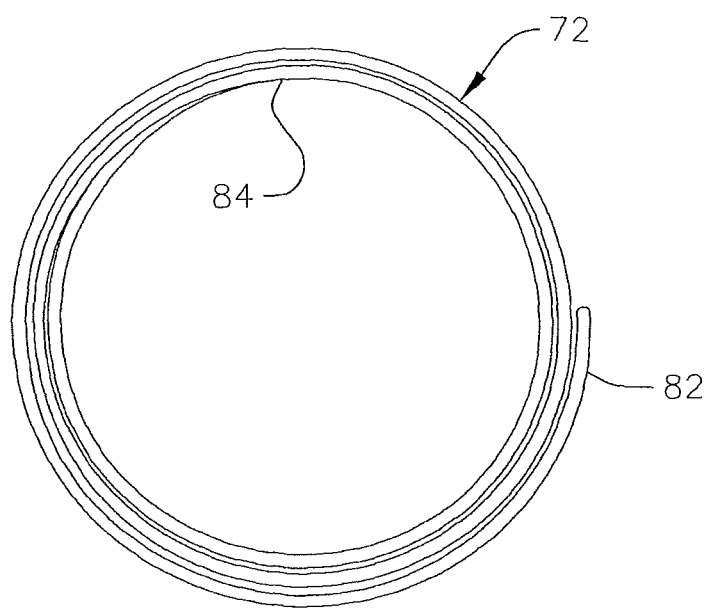

A helical anchor according to an embodiment of the invention is constructed as seen in FIGS. 3A to 3E. FIG. 3A shows a perspective view of a helical anchor 72, FIG. 3B shows a side view of the anchor 72, and FIG. 3C shows a top view of the anchor 72. The helical anchor 72 includes a coil with a plurality of turns extending along a central axis of the anchor. The anchor 72 has a series of lower turns or coils 82 and a series of upper turns or coils 84. The individual turns of the lower coils 82 are spaced apart from one another by small gaps. Meanwhile, the individual turns of the upper coils 84 are wound more closely to one another. In addition, the turns of the lower coils 82 have a larger radius of curvature than the turns of the upper coils 84, and therefore form a larger inner annular space. These features will be discussed in more detail below with respect to implantation of the anchor 72 at a native mitral valve. In other embodiments, the characteristics and differences between the lower coils 82 and the upper coils 84 of the anchor 72 can be arranged differently based on, for example, the anatomy of the patient.

Figure 1:
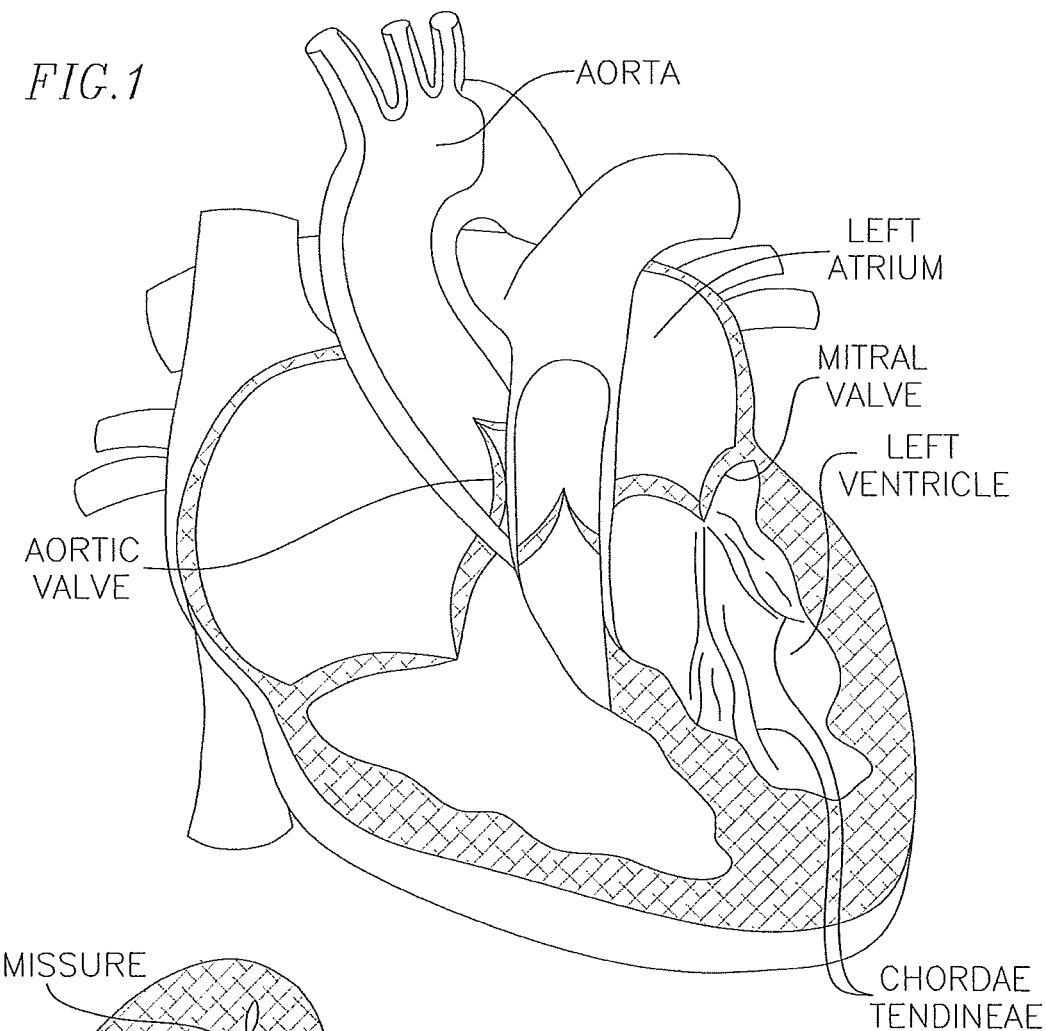
FIG. 1 shows a schematic cross-sectional view of a human heart.
Figure 2:
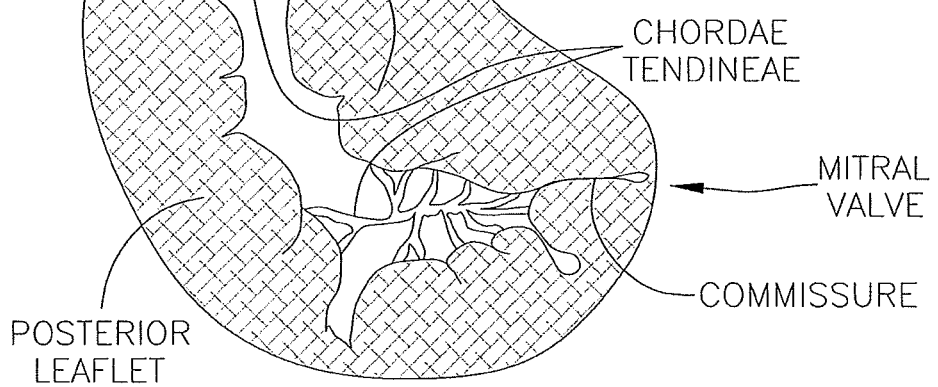
FIG. 2 shows a schematic top view of the mitral valve annulus of a heart.
Figure 3D:
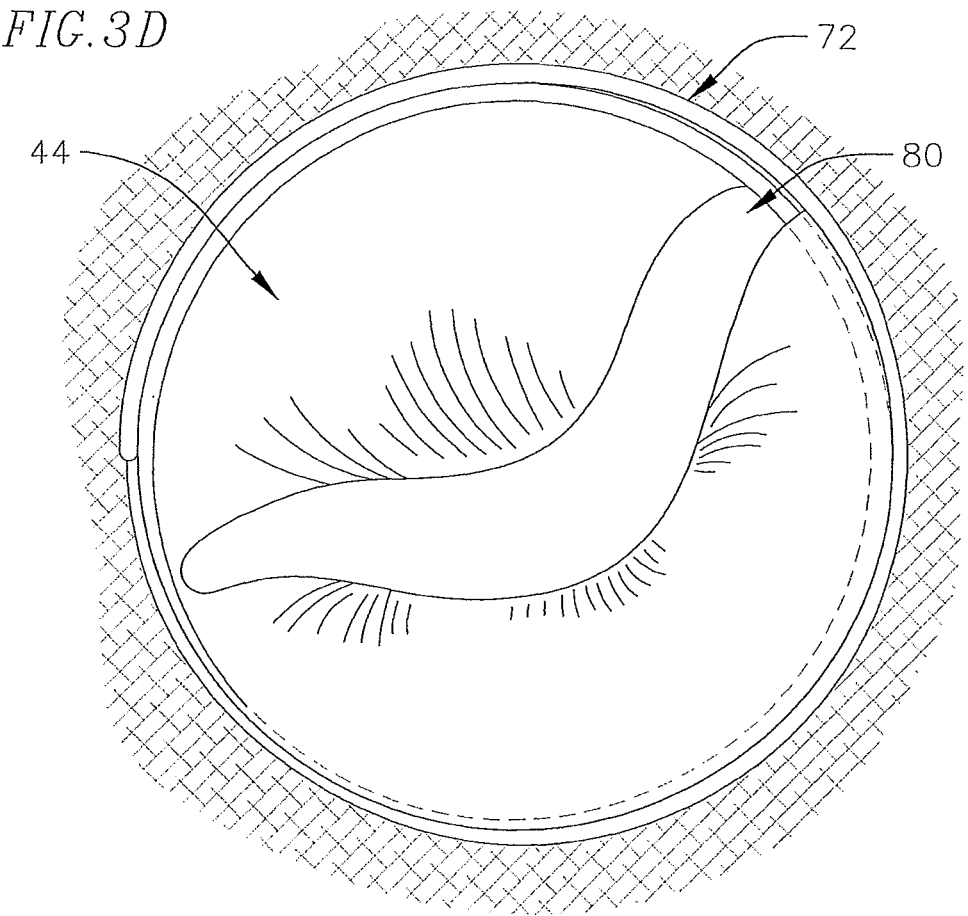
Figure 3E:
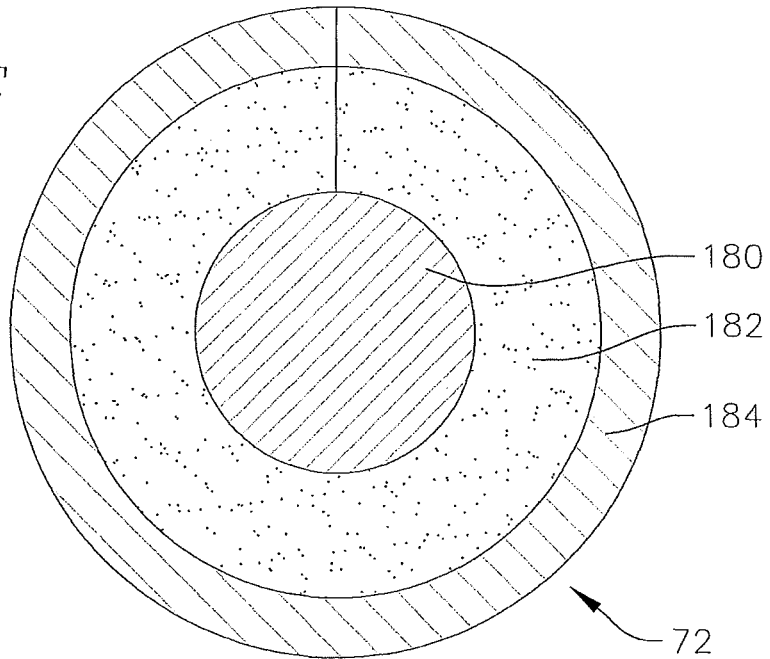

As can be seen most clearly in FIG. 3C, the anchor 72 twists or coils around a central axis of the anchor 72 to provide a generally circular or cylindrical space therein that can more easily hold and anchor a circular valve prosthesis than can the non-circular shape of the native mitral valve annulus seen in FIG. 2. Therefore, as can be seen in FIG. 3D, when a helical anchor 72 is positioned about a mitral valve 44, the helical anchor 72 provides a more solid and structurally stable docking station or site for docking or coupling valve prostheses to the native mitral valve annulus. Passage of a portion of the anchor 72 at a commissure 80 of the mitral valve 44 (as seen in FIG. 3D, the process of which will be discussed in greater detail below) allows for placement of the anchor 72 both above and below the mitral valve annulus, for more secure anchoring of a valve prosthesis therein. In addition, a smallest inner space defined by the coils of the anchor 72 can be undersized relative to an expanded diameter of a valve prosthesis, such that a radial pressure is generated between the anchor 72 and the valve prosthesis when the prosthesis is expanded therein.

In one embodiment, a core 180 of the helical coil 72 is constructed of or includes a shape memory material, such as Nitinol. However, in other embodiments, the core 180 of the helical coil 72 can be made of or include other bio-compatible materials, for example, other alloys, or for example, metals such as titanium or stainless steel. In some embodiments, the coil can have enlarged and/or rounded ends, for example, to prevent tips at ends of the coil 72 from damaging surrounding tissue during deployment. As can best be seen in FIGS. 3A, 3B, and 3E, the last of which illustrates a cross-section of a portion of the helical coil 72, the core 180 of the coil 72 is covered or surrounded by a foam layer 182 and a cloth cover 184. In the embodiment shown, the foam layer 182 is a Biomerix foam layer, for example, a 2 millimeter thick layer of polyurethane sheet material, and the cloth cover 184 is made of or includes a polyester material. In the illustrated embodiment, the respective ends of the foam layer 182 and cloth cover 184 meet circumferentially around the coil core 180 at substantially the same place. However, in other embodiments, the foam layer 182 and cloth cover 184 are wrapped around the coil core 180 and attached at different circumferential points around the coil core 180. The layers 182, 184 can be attached together to the coil core 180, or can be attached separately to the coil core 180.

In greater detail, in some embodiments, the fabric or cloth cover 184 that covers the helical coil is, for example, a polyethylene terephthalate (PET) polyester material. The fabric can have a thickness of 0.008±0.002 inches, and can have density characteristics of, for example, 2.12±0.18 oz/yd$^2$, 40±5 wales/inch, and 90±10 courses/inch. The fabric layer can further be cut to have a length or width of approximately 13+1/−0.5 inches in order to cover substantially an entire length of the helical coil 72.

In some embodiments, the foam layer 182 can be cut to 19 mm×5 mm, and the cloth cover 184 can be cut to 19 mm×6 mm. However, other sized cuts of the various layers 182, 184 can also be utilized, depending on for example, the size of the helical coil, the thickness of the respective layers, and the amount of each layer intended for covering the core 180. In some embodiments, the foam layer 182 can be attached to the cloth cover 184 using, for example, 22 mm of polytetrafluoroethylene (PTFE) suture with a light straight stitch. The foam layer 182 and/or the cloth cover 184 can be folded around the coil core 180 and cross-stitched to the core 180 using, for example, 45 mm of fiber suture. However, the invention should not be limited to these attachment properties, and other suture sizes and/or types, or any of various other attachment means or methods for effectively attaching the foam layer 182 and/or the cloth cover 184 to the coil core 180, can also be utilized and implemented. For example, in some embodiments, the core can be a modified core with through holes, notches, or other features that can be laser cut or otherwise formed along the core. Such features in the core can be used to interact with sutures, to increase friction, or to otherwise help hold a cover layer or layers against the core and prevent or restrict sliding or other relative movement between the cover layer and the core. In some embodiments, the core can also be formed to have a non-circular cross-section to increase a contact area between the core and the cover layer. For example, a flat wire coil can be used to form the core. Additionally, various bio-compatible adhesives or other materials can be applied between the core and the cover layer in order to more securely hold a position of the cover layer relative to the core. In some embodiments, a hydrogel or other material that expands upon contact with blood can be applied between the core and the cover layer as a gap filler to create a stronger seal or interference fit between the core and the cover layer.

Figure 4A:
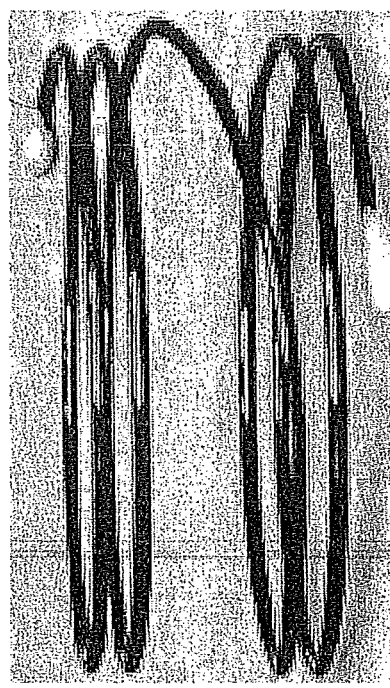
FIGS. 4A and 4B are respective images of an uncovered coil and a covered coil according to an embodiment of the invention.
Figure 4B:
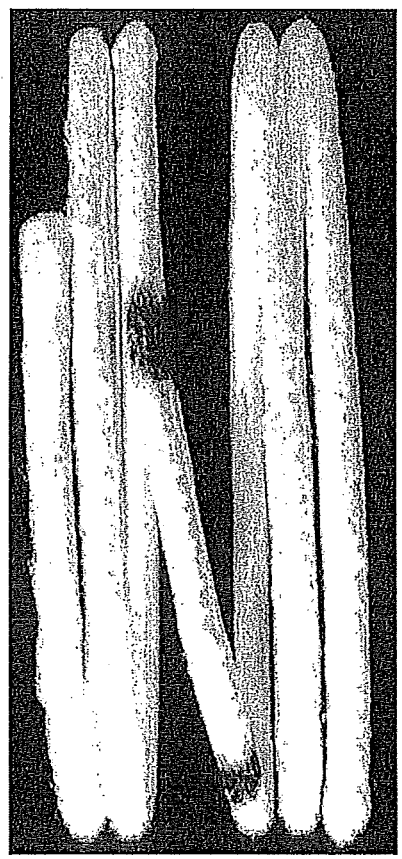

FIG. 4A shows a core of one embodiment of a helical anchor prior to applying a foam and/or fabric cover thereupon, and FIG. 4B shows a covered helical anchor, with a foam layer and a fabric layer, similarly as described with respect to FIGS. 3A to 3E. The foam and/or fabric layers are bio-compatible, and generally serve to promote ingrowth of the surrounding tissue around and into the anchor, to further secure the anchor about the mitral valve annulus after the anchor and valve have been implanted. While in the above described embodiments, both a foam layer and a fabric layer are applied onto an alloy core of the helical anchor, in other embodiments, only a foam layer is applied onto the core of the anchor, while in still other embodiments, only a fabric layer is applied onto the anchor core.

According to embodiments of the invention, mitral valve replacement can be performed in various different manners. In one procedure using catheters, an anchoring or docking station as described above and/or a prosthetic valve to be positioned in the anchor (which may initially be compressed or collapsed radially) can be delivered through blood vessels to the implant site. This can be accomplished, for example, through arteries or veins connected to various chambers of the heart. In one exemplary embodiment (as will be seen in FIGS. 6A to 6D), a catheter can be delivered through the inferior vena cava into the right atrium, and then through a transseptal puncture to reach the left atrium above the mitral valve.

In some cases, mitral valve replacement may not be purely performed percutaneously through remote arteries and/or veins, and a more open procedure may be necessary. In these cases, for example, practitioners can make a small chest incision (thoractomy) to gain access to the heart, and then place catheter-based delivery devices and/or the implants directly into the heart.

Figure 5A:
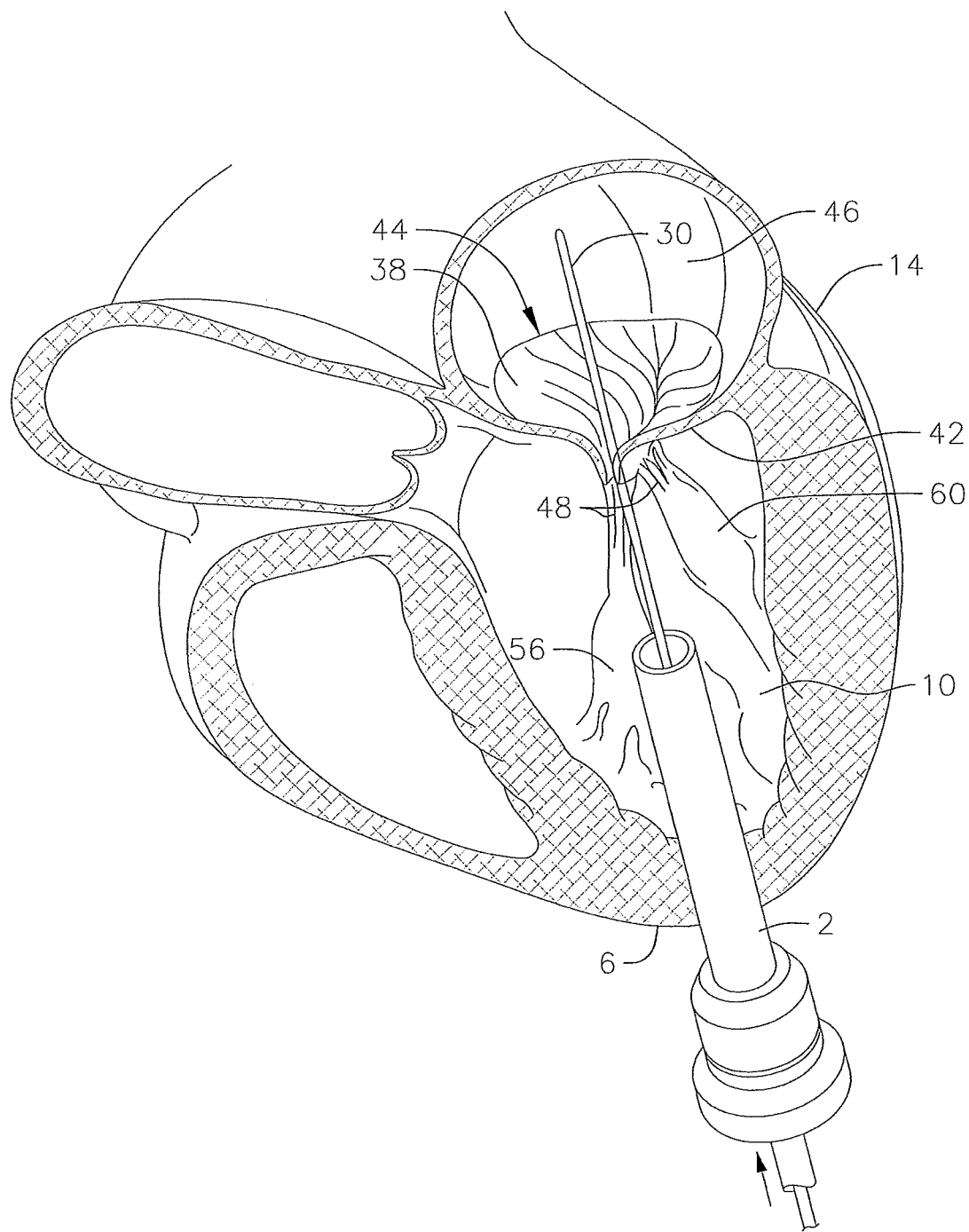
FIGS. 5A to 5F show a process of deploying a helical coil anchor via a transapical procedure according to an embodiment of the invention.

Referring now to the embodiment in FIGS. 5A to 5F, a transapical procedure for positioning a coiled or helical anchor in the mitral position of a patient's heart is shown. In this example, the anchor is delivered to the mitral position from the apex of the heart and through the left ventricle. FIG. 5A shows an introducer 2 inserted into the left ventricle 10 of a patient's heart 14 through an incision at the apex 6. To prevent blood leakage through the apex 6, a purse string suture can be tightened around the introducer 2, or an occluder device can be used, among other options. A guide wire 30 is advanced from the introducer 2 through the left ventricle 10, past the papillary muscles 56, 60 and the chordae tendineae 48, and between the anterior and posterior leaflets 38, 42 of the native mitral valve 44, such that a portion of the guide wire 30 is positioned in the left atrium 46.

Figure 5B:
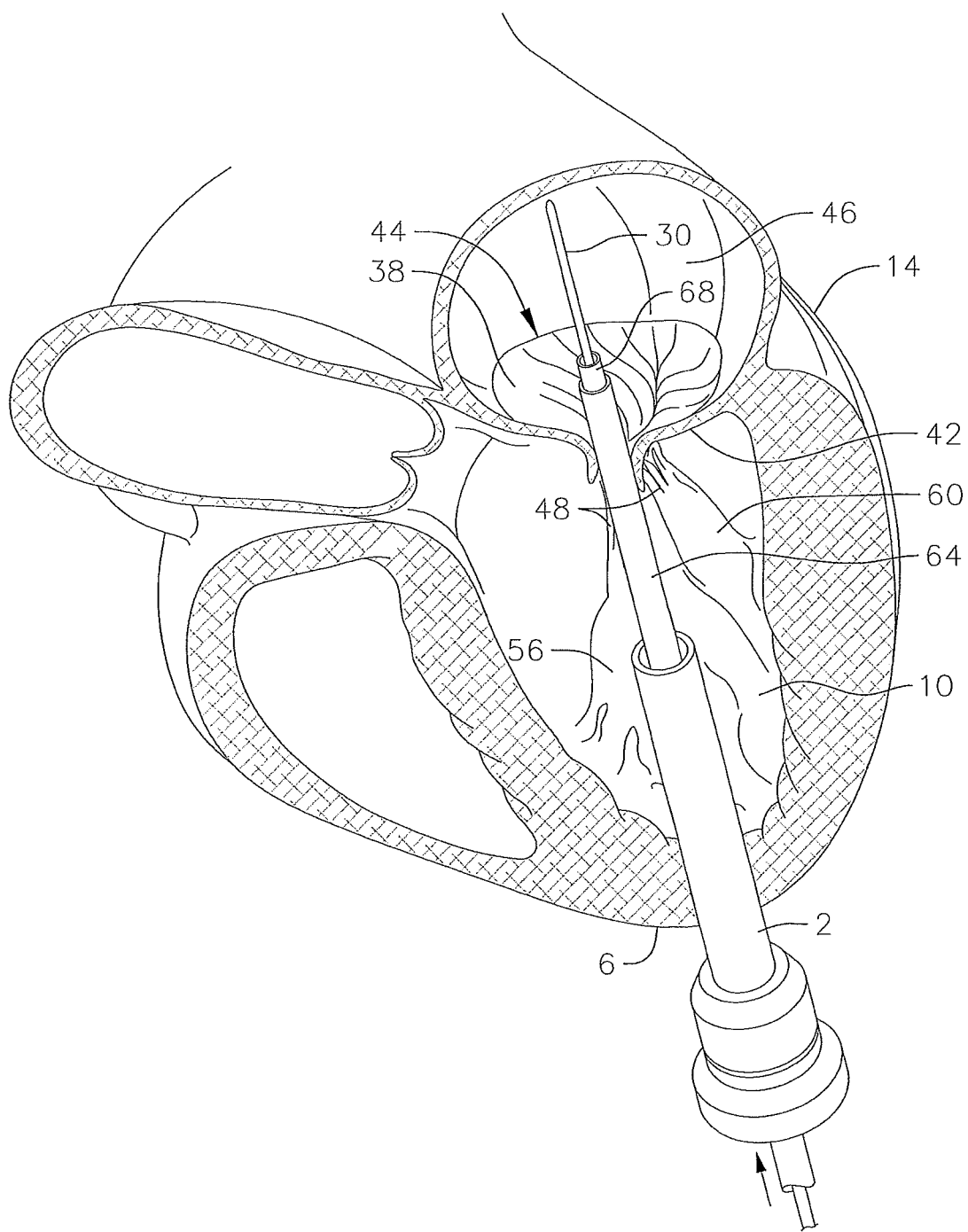

As shown in FIG. 5B, a delivery catheter 64 is then introduced over the guide wire 30 into the left atrium 46. The delivery catheter 64 facilitates the later introduction of a coil guide catheter 68, which has a pre-formed curved shaped designed to assist in the introduction of a coiled or helical anchor 72. The coil guide catheter 68 is straightened for introduction through the delivery catheter 64, which can be, in contrast, substantially straight and which can be made of a stiffer material than the coil guide catheter 68. Therefore, upon exiting the delivery catheter 64, the distal end of the coil guide catheter can deflect or revert to its original pre-formed curved shape to assist with proper introduction and positioning of the helical anchor 72. The guide wire 30 can be retracted and removed during the process of deploying and positioning the coil guide catheter 68, prior to delivery of the helical anchor 72.

In other embodiments, the coil guide catheter 68 can be introduced into the heart as a relatively straight element, and can then be manipulated to take on the desired curved shape.

Figure 5C:
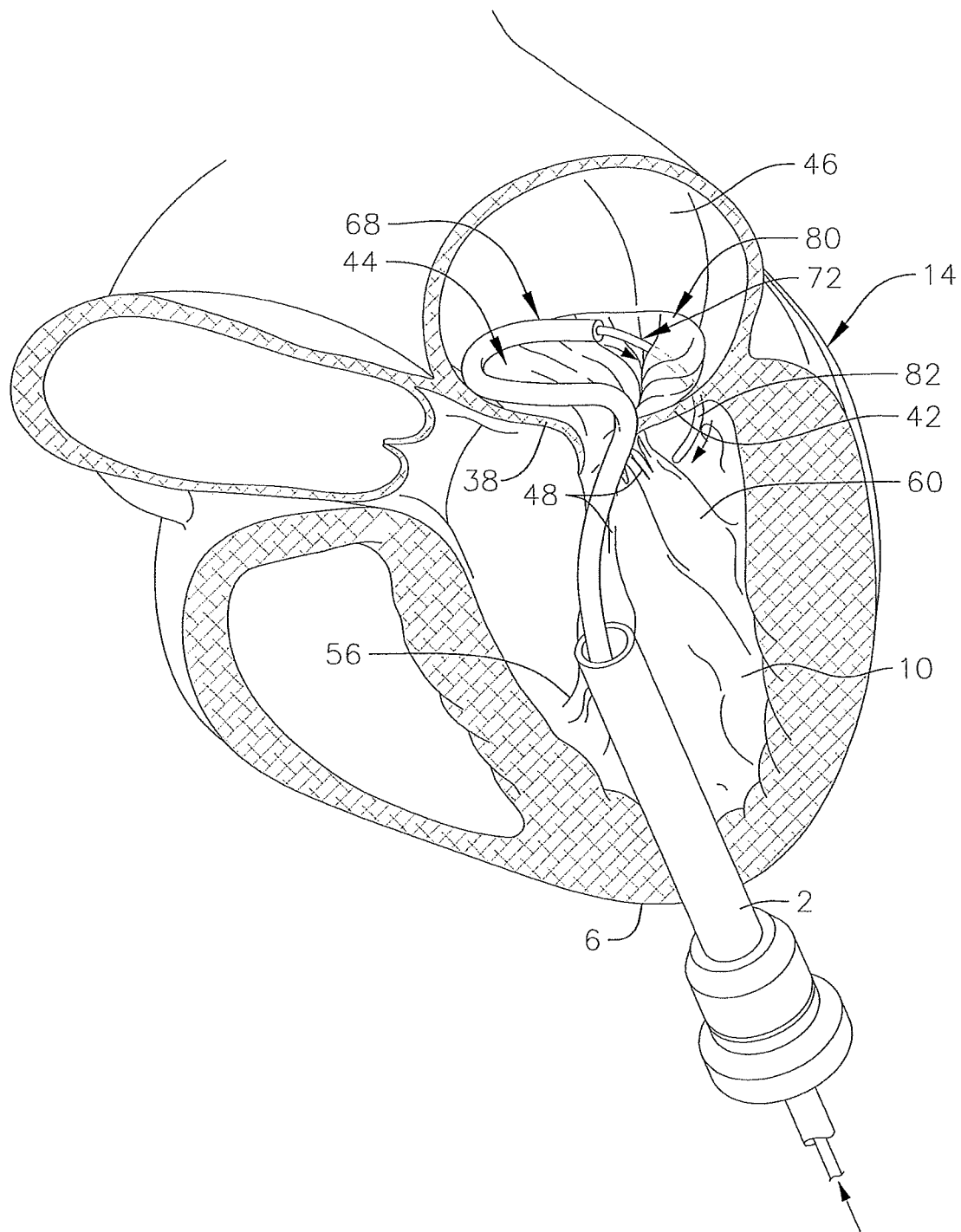

As shown in FIG. 5C, in an initial coil delivery position, the delivery catheter 64 has been removed, and the distal end of the coil guide catheter 68 is positioned in the left atrium 46, near one of the mitral valve commissures 80, where the anterior mitral valve leaflet 38 meets the posterior mitral leaflet 42 near a perimeter of the mitral valve 44. In other embodiments, the distal end of the coil guide catheter can instead be positioned in the left ventricle 10 near the mitral valve. In FIG. 5C, the distal tip of the lower coils 82 of the helical anchor 72 can be seen extending out of the distal end of the coil guide catheter 68, and through the mitral valve back into the left ventricle 10. The tip of the anchor 72 can have a slight downward turn or bend to facilitate the initial insertion and advancement of the tip back at a commissure 80 of the mitral valve 44.

Figure 5D:
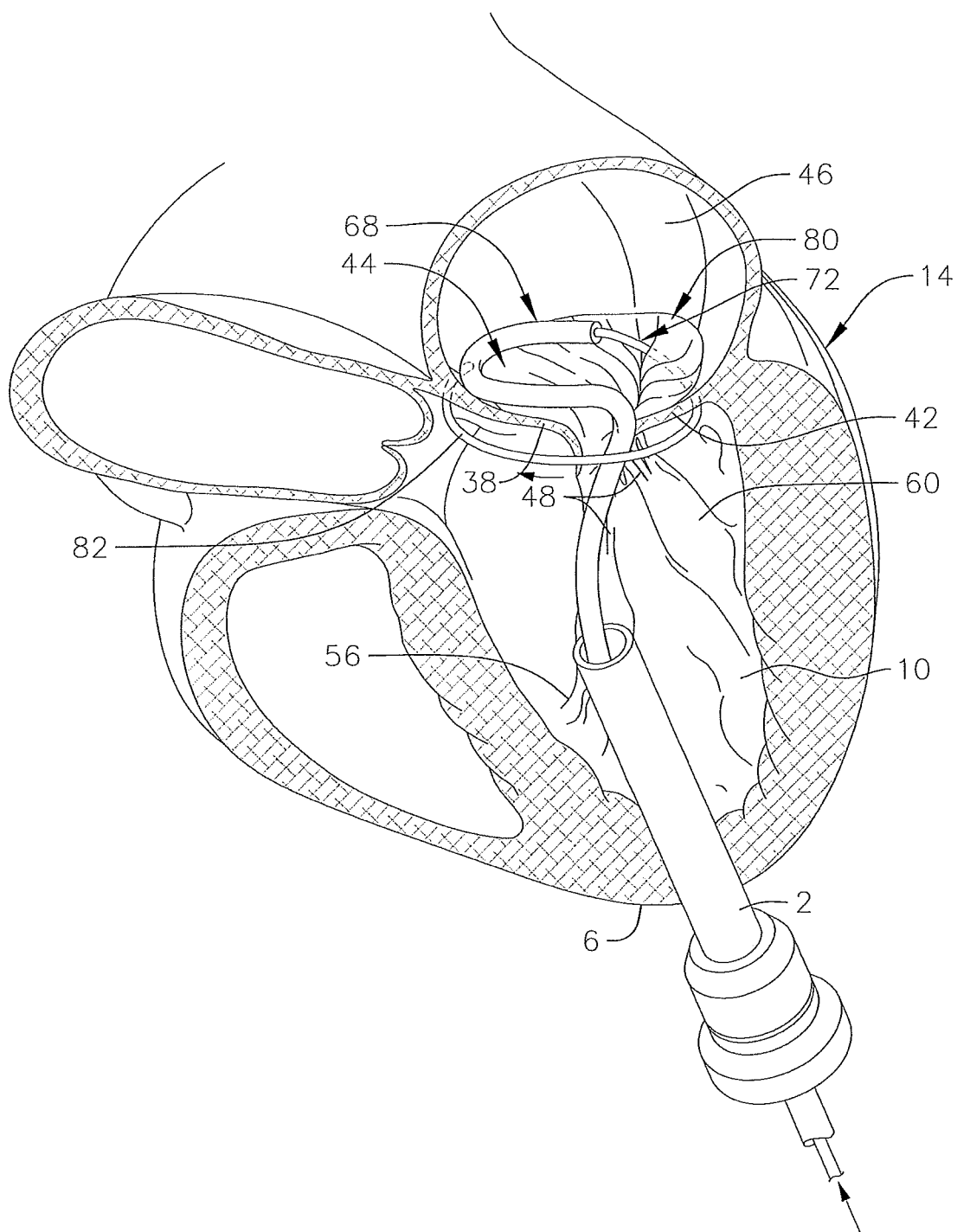

The helical anchor 72 is then further advanced by being pushed through the coil guide catheter 68. FIG. 5D shows the helical anchor 72 being advanced and twisting under or around the leaflets 38, 42 of the mitral valve 44. The helical anchor 72 is directed to go entirely around the leaflets 38, 42 of the mitral valve 44, as well as the chordae tendineae 48. The lower coils 82 of the anchor 72 can therefore be made slightly larger, to facilitate easier corralling or directing of the anchor 72 around the leaflets 38, 42, and the chordae 48 during anchor deployment. Additionally, the turns of the lower coils 82 can be spaced slightly apart from another, for easier advancement of the coils 82 through the native valve 44 at the commissure 80. Meanwhile, smaller coils, such as those of upper coils 84, can help more securely or tightly hold a valve prosthesis.

Figure 5E:
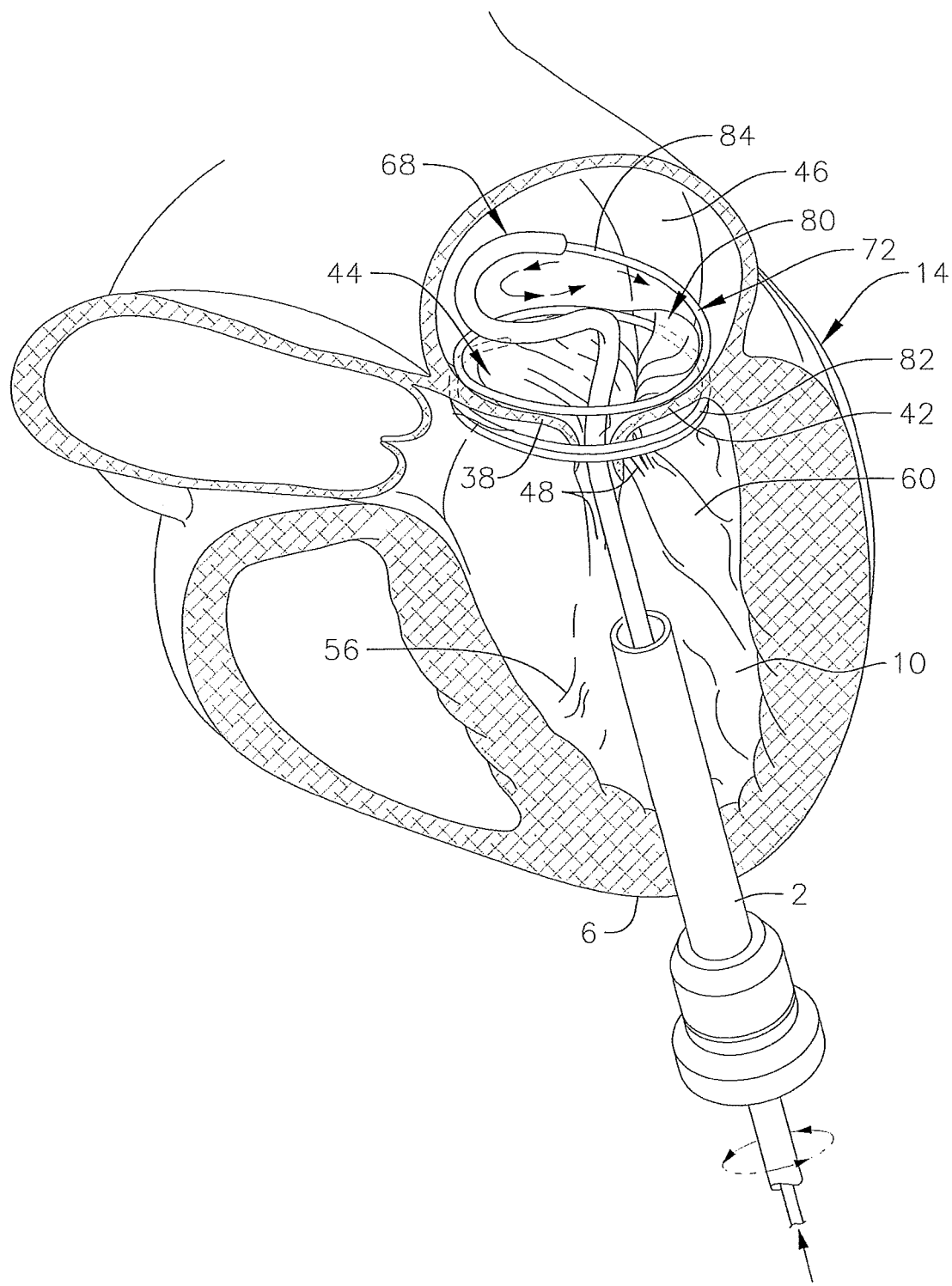

After the lower coils 82 of the anchor 72 have been placed under the mitral valve annulus, as seen in FIG. 5E, the upper coils 84 of anchor 72 are then deployed from the coil guide catheter 68. In some embodiments, after the lower coils 82 have been advanced under the mitral valve annulus to a desired position, it may not be desirable to further push or advance the coil 72, in order to keep or maintain the orientation and positioning of the lower coils 82 in the left ventricle 10. Therefore, the upper coils 84 of the anchor 72 can be deployed in the left atrium 46 by rotating the coil guide catheter 68 backwards (as illustrated by the arrows at the bottom of FIG. 5E), in order to reveal and deploy more of the coil anchor 72 from within the catheter 68. Other embodiments deploy and position the upper coils 82 of the anchor 72 in various different ways.

Figure 5F:
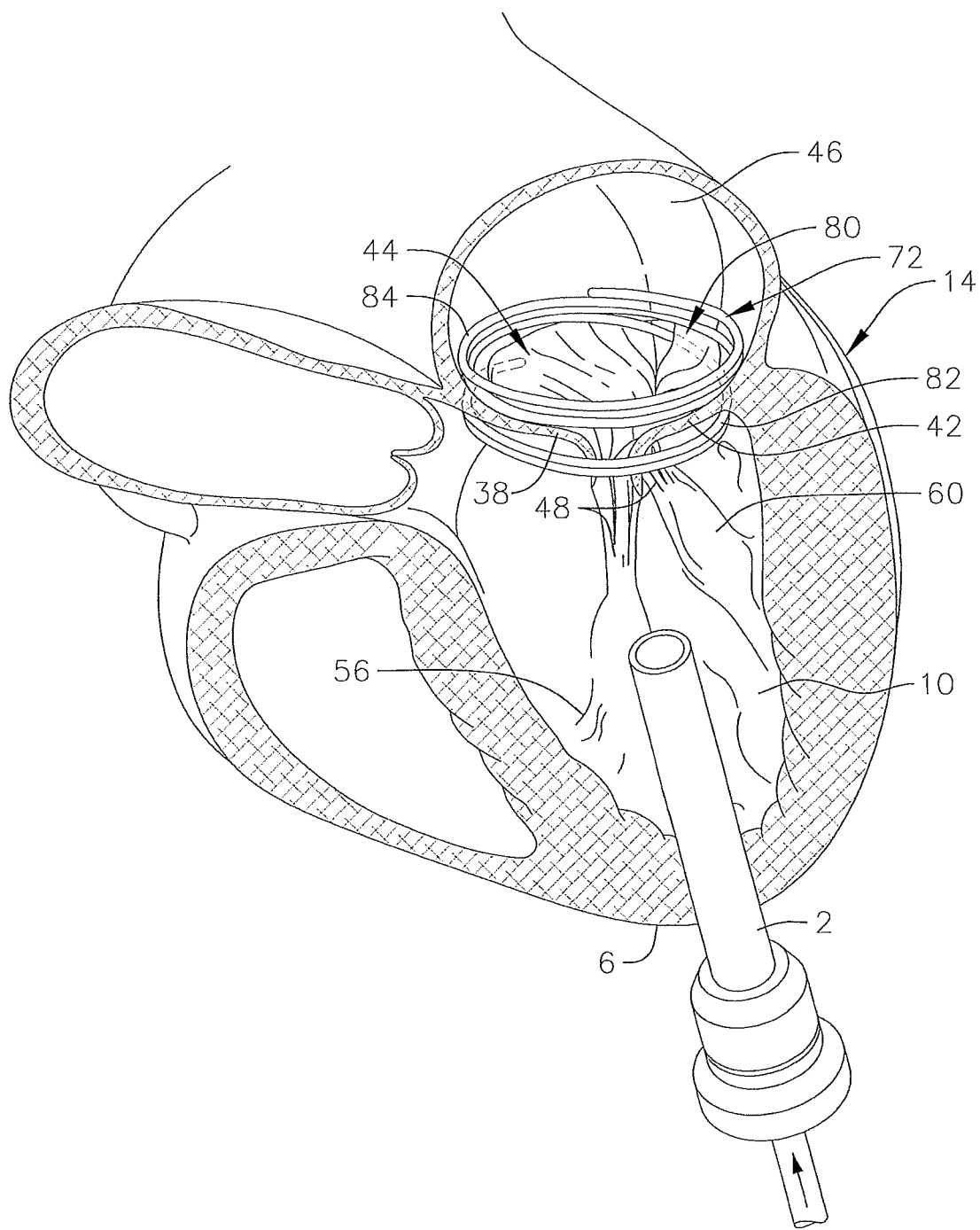

After the helical anchor 72 is fully implanted, the coil guide catheter 68 is removed, as can be seen in FIG. 5F. While the deployed anchor in FIG. 5F has about three coils positioned above the mitral valve 44 and two coils positioned below the mitral valve 44, other embodiments can have other different arrangements and coil positionings based on the specific application.

It should also be noted that once a helical anchor 72 is inserted and positioned as described above, and prior to implantation of a prosthetic valve therein, the native mitral valve 44 can continue to operate substantially normally, and the patient can remain stable. Therefore, the procedure can be performed on a beating heart without the need for a heart-lung machine. Furthermore, this allows a practitioner more time flexibility to implant a valve prosthesis within the anchor 72, without the risk of the patient being in a position of hemodynamic compromise if too much time passes between anchor implantation and valve implantation.

FIGS. 6A to 6D show an alternative procedure for positioning a helical anchor in the mitral position of a patient's heart. In this example, an anchor 330 is delivered to the mitral position through the atrial septum of the heart. In an example procedure, a catheter 332 is introduced into a patient's venous system by percutaneous puncture or by a small surgical cut, for example, at the patient's groin. Alternative access sites can also be used.

Figure 6A:
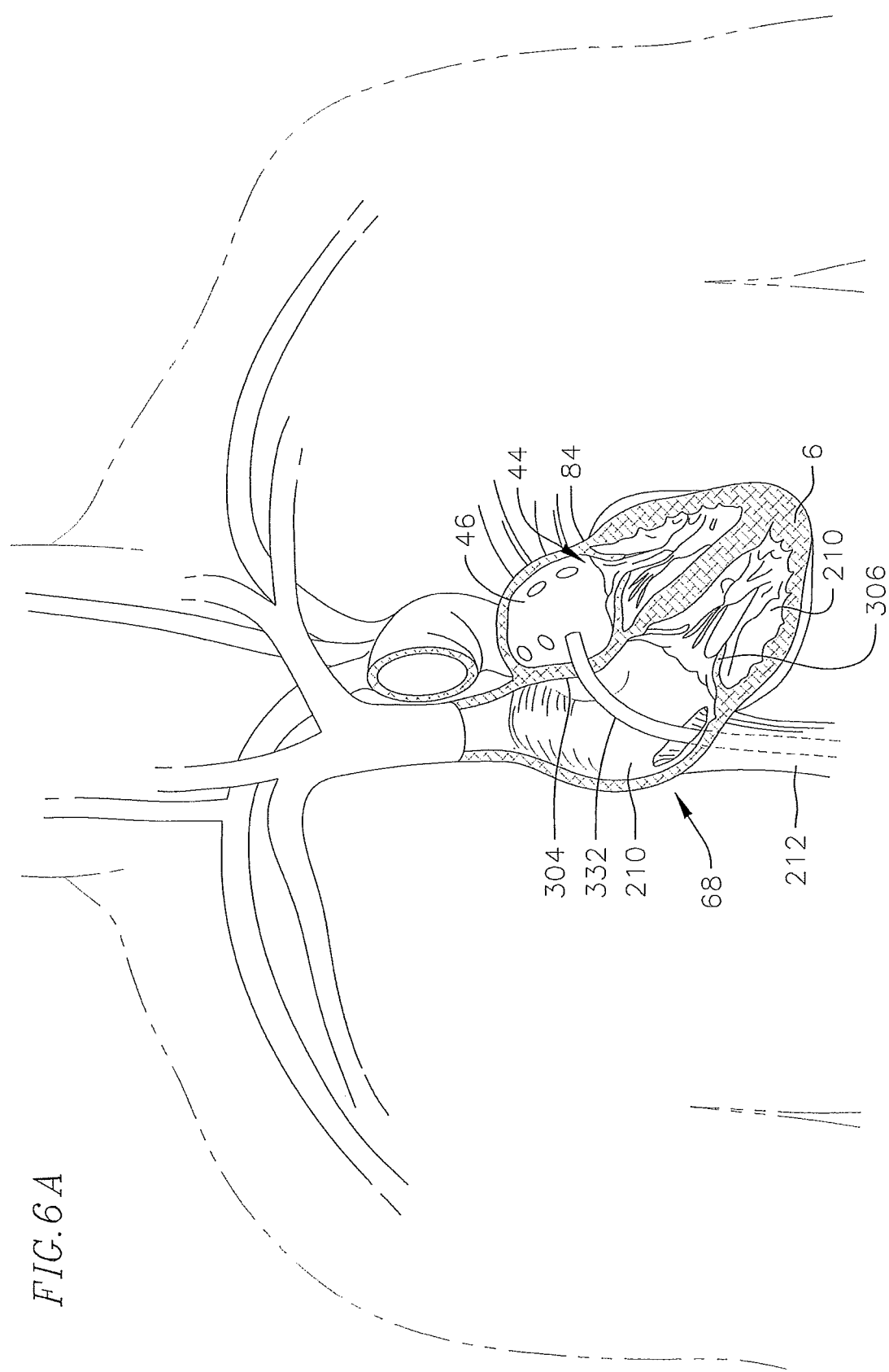
FIGS. 6A to 6D show a process of deploying a helical coil anchor via a transseptal procedure according to another embodiment of the invention.
Figure 6B:
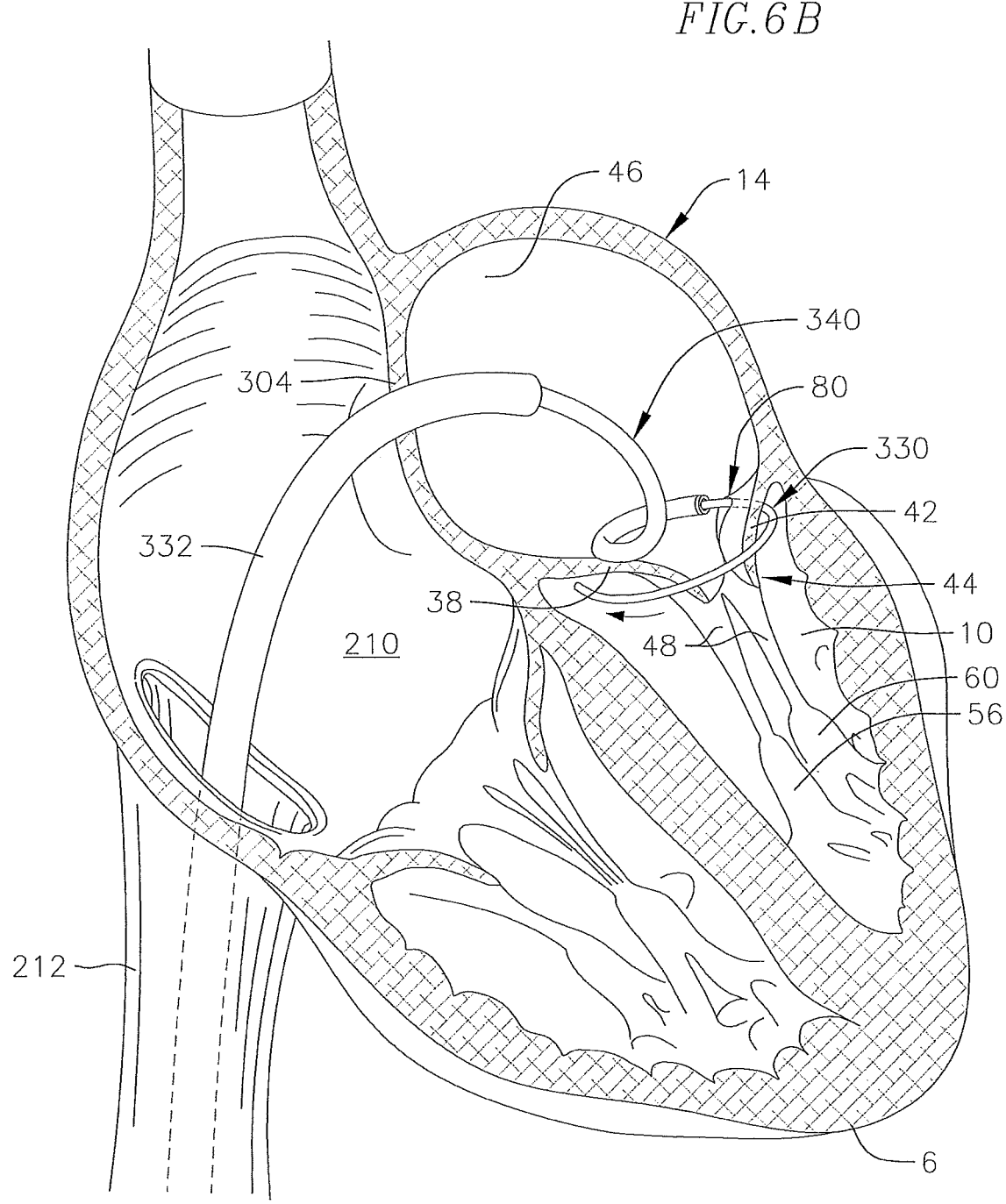

As shown in FIG. 6A, the catheter 332 is advanced up the inferior vena cava 212, into the right atrium 210, across the atrial septum 304, and into the left atrium 46. Then, in FIG. 6B, a coil guide catheter 340 is deployed from a distal end of the catheter 332 and extends to a position in the left atrium 46 near a commissure 80 of the mitral valve 44, similarly as seen in the embodiment in FIGS. 5A-5F. The anchor 330 exits the tip of the coil guide catheter 340 and is advanced under the mitral valve 44 at the commissure 80.

Figure 6C:
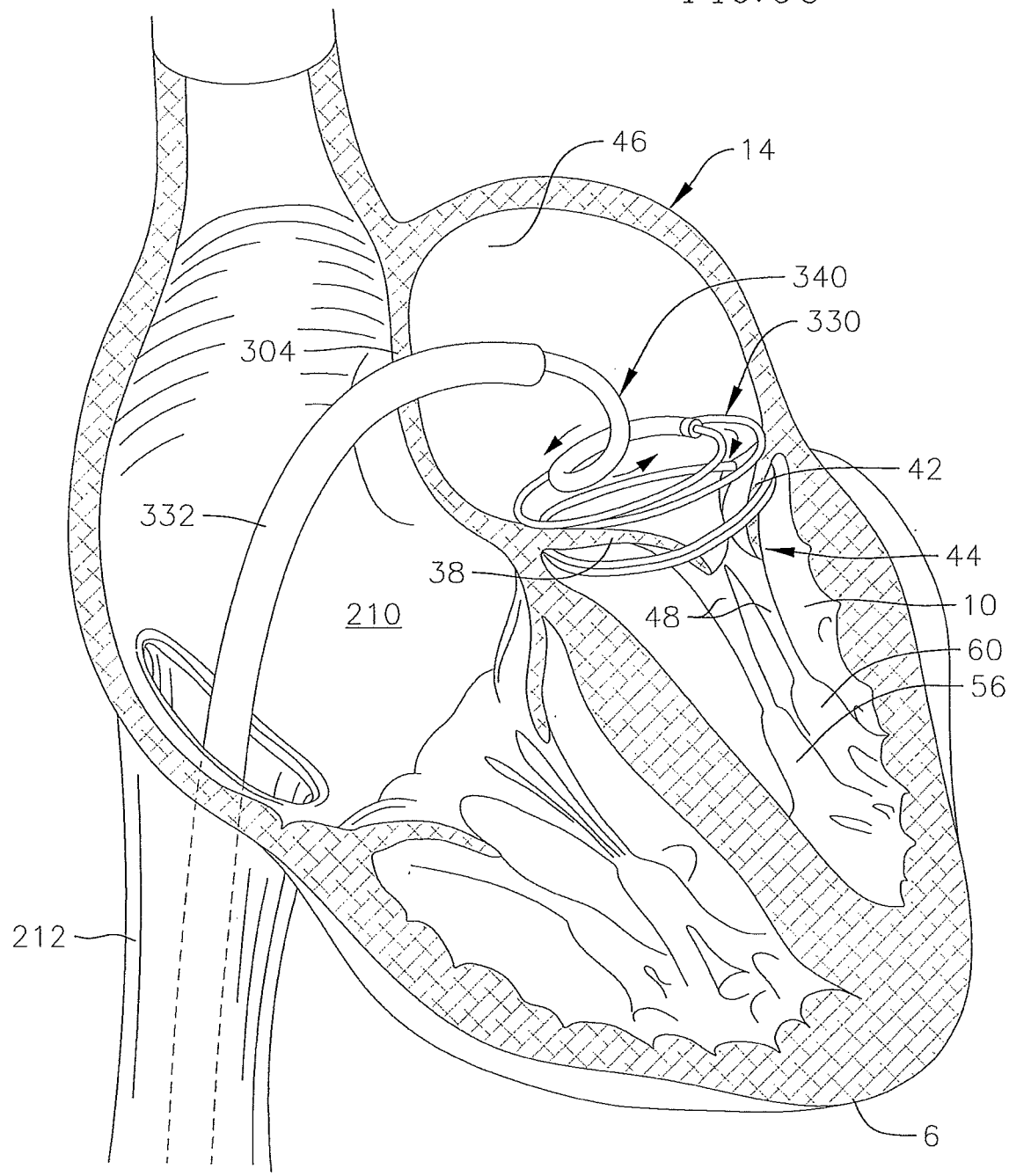
Figure 6D:
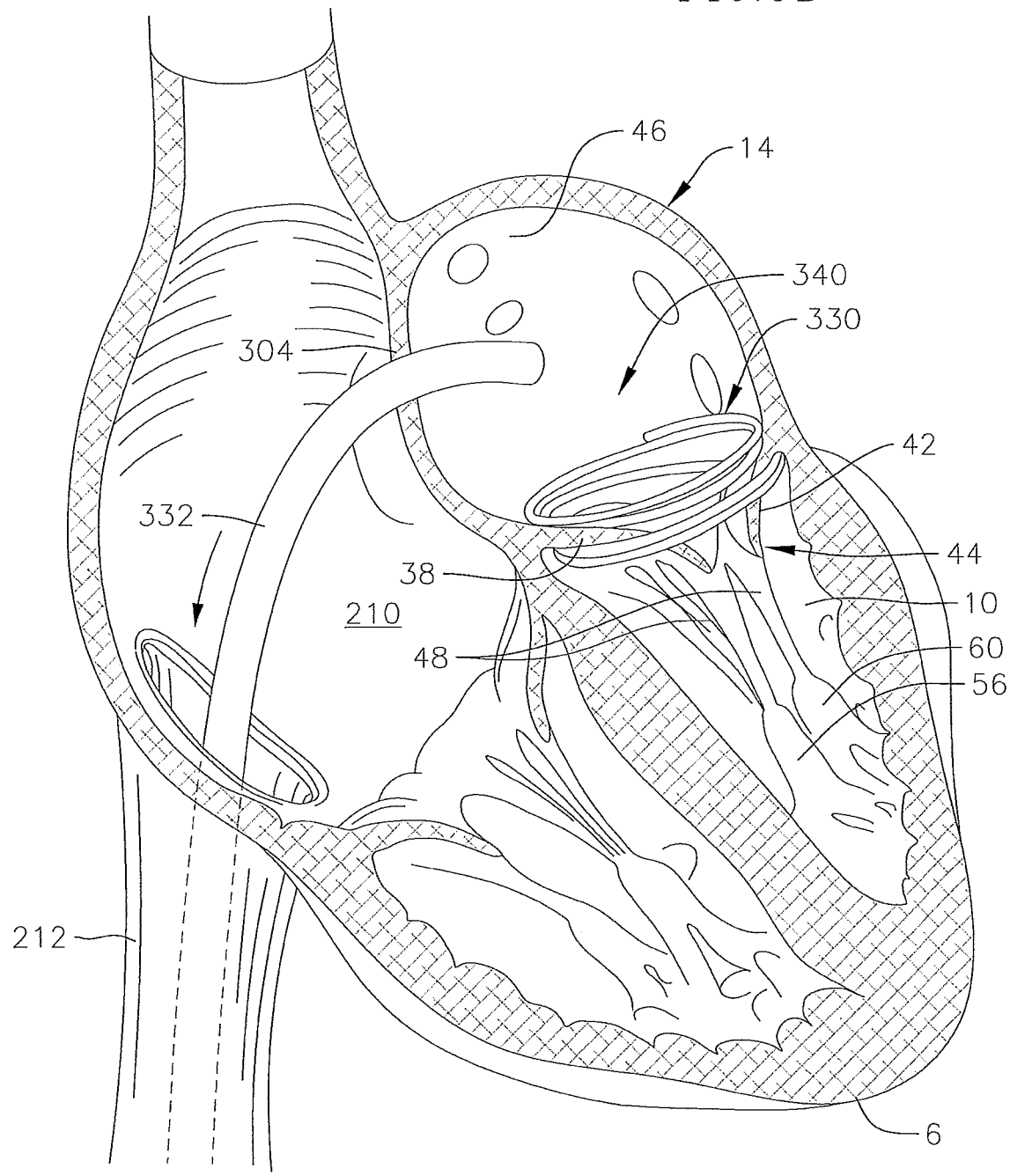

After the lower coils of the anchor 330 have been positioned under the mitral valve 44 to a desired orientation, the upper coils of the anchor 330 can then be deployed from the coil guide catheter 340, for example, by rotating the coil guide catheter 340 in the opposite direction of advancement of the anchor 330, as shown in FIG. 6C. After the helical anchor 330 is implanted and placed in a desired position, the coil guide catheter 340 is removed, as seen in FIG. 6D.

Figure 7A:
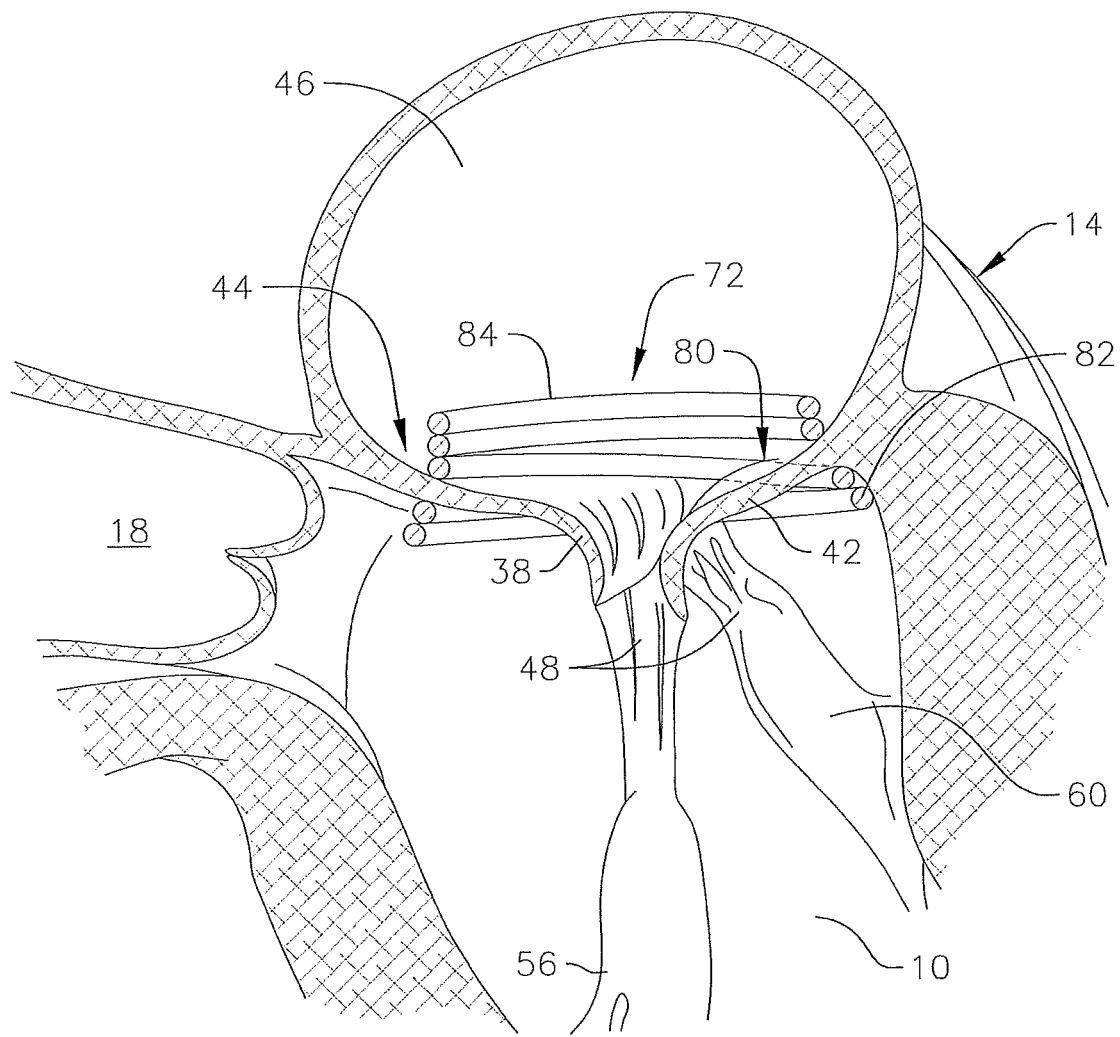
FIGS. 7A and 7B show side cross-sectional views of a helical coil anchor deployed in the mitral position, with and without an implanted valve prosthesis, respectively, according to an embodiment of the invention.
Figure 7B:
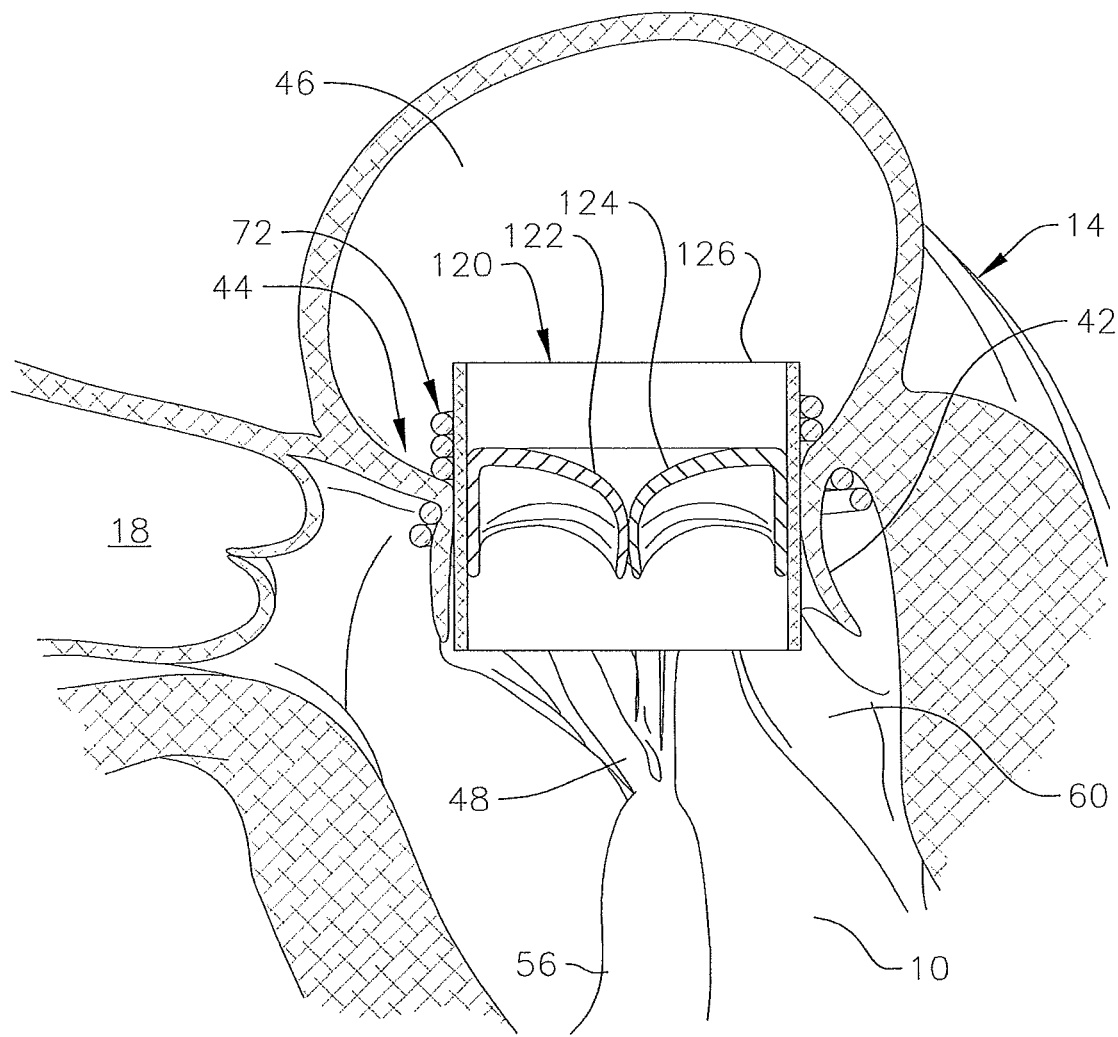

FIG. 7A shows a side cross-sectional view of a helical anchor 72 that has been implanted in a mitral position of a patient's heart, and FIG. 7B shows a side cross-sectional view of a helical anchor 72 with a valve prosthesis 120 retained therein. Orientations, shapes, and size differentials between the different coils of the anchor 72 other than those illustrated may also be employed for various reasons, for example, to cause ends of the anchor 72 to push against the ventricular and/or atrial walls, in order to better hold a position of the helical anchor 72.

In FIG. 7B, a valve prosthesis 120 is retained by the helical anchor 72 in the mitral position. The valve prosthesis 120 is preferably a modified or unmodified transcatheter heart valve, such as, for example, the Edwards Lifesciences Sapien™ valve. Generally, the valve prosthesis 120 will include an expandable frame structure 126 that houses a plurality of valve leaflets 122, 124. The expandable frame 126 can be self-expanding, or can be, for example, balloon expandable, and can be introduced through the same introducer and/or catheters used to introduce the anchor 72, or may be introduced through a separate catheter.

In embodiments of the invention, a collapsed valve prosthesis 120 is first positioned in a central passage or inner space defined by the anchor 72, and is then expanded to abut against and dock in the anchor 72. In these embodiments, at least a portion of the leaflet tissue 38, 42 of the mitral valve 44 is secured or pinned between the anchor 72 and the valve prosthesis 120 to lock the anchor 72 and valve prosthesis 120 in position and prevent them from shifting or dislodging. The tissue of leaflets 38, 42 also creates a natural seal to prevent blood flow between the valve prosthesis 120 and the helical anchor 72. As discussed above, in some embodiments, a smallest inner diameter defined by the coils of the anchor 72 is smaller than a diameter of the valve prosthesis 120 after it has been expanded, such that a radial resistance force is formed between the anchor 72 and the valve prosthesis 120, which further secures the parts together. Pressure between the anchor 72 and the valve prosthesis 120 can occur either above or below the mitral valve 44, or both. Due to the pressure formed between the anchor 72, the valve prosthesis 120, and the leaflets 38, 42 therebetween, generally no additional sutures or attachments between the valve prosthesis 120 and the anchor 72 or the adjacent heart tissue is needed. Due to the different materials used for the anchor 72 and the prosthesis 120, a circumferential friction force is also generated between parts of the anchor 72 and the prosthesis 120 that contact one another, thereby restricting uncoiling and expansion of the anchor 72. This interaction will be discussed in greater detail below, with reference to FIGS. 9A and 9B.

Figure 8A:
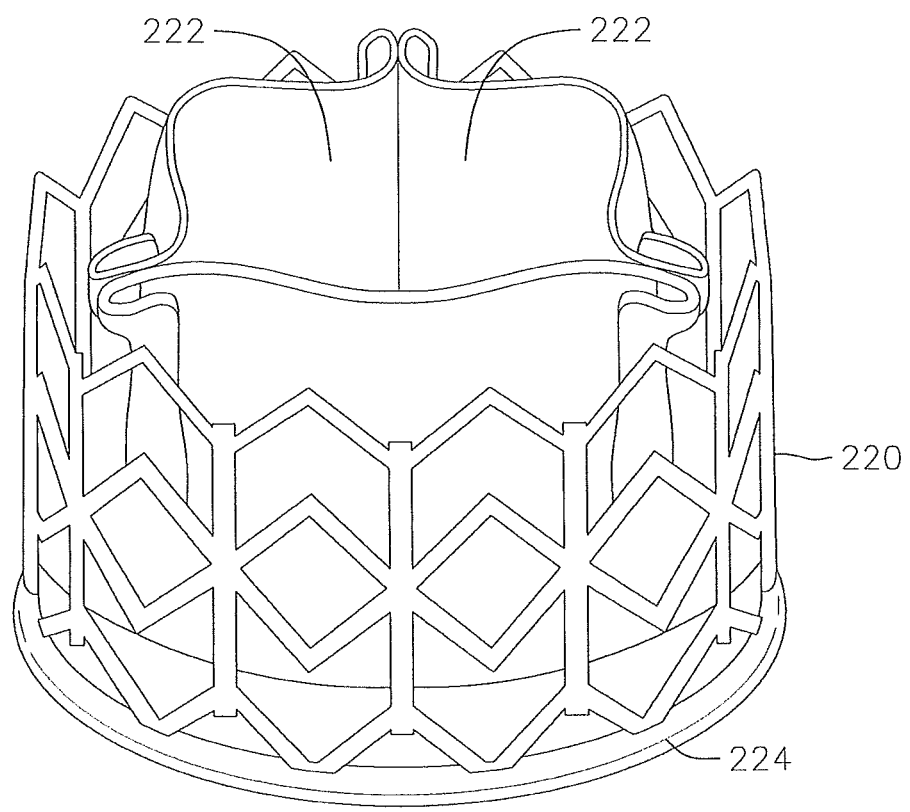

FIGS. 8A-8B show an embodiment of a prosthetic heart valve for use with a helical anchor as previously described. Preferably, the valve prosthesis used with the helical anchor is, for example, a modified or unmodified transcatheter heart valve, such as the Edwards Lifesciences Sapien™ valve. FIG. 8A shows a valve having an expandable frame structure 220 and a plurality of valve leaflets 222. The frame 220 of the prosthetic valve can be self-expanding and can be made of, for example, a shape memory material such as Nitinol, or alternatively, can be made of a non-shape memory material. In some embodiments, the valve prosthesis is balloon expandable, and is intended for expansion within a previously positioned helical anchor. The leaflets 222 can be made from, for example, pliable animal tissues such as cow, pig, or horse pericardium or valve tissue, or from any other suitable material.

Attached or integral along a distal or lower end of the frame 220, the valve prosthesis further includes an annular ring or cuff 224 which is made of or generally includes materials that are less rigid than the materials of the frame 220. FIG. 8A only schematically shows a shape of the annular cuff 224 for simplicity, without additional attachment features, while FIG. 8B shows a cross-section of a lower portion of a valve prosthesis that includes additional attachment features, such as a sleeve 246 that holds the cuff in place on the frame. In the embodiment shown in FIG. 8B, the annular cuff 224 substantially surrounds at least the bottom corners 226 of the expandable stent frame 220 of the valve prosthesis. The annular cuff 224 includes a foam layer 242 surrounding the bottom corners 226 of the frame 220, a fabric layer 244 covering the foam layer 242, and an additional cuff retention sleeve or layer 246 for holding the foam layer 242 and the fabric layer 244 in place. One or more stitches or sutures 248 are made between the sleeve layer 246 and one or more portions of the frame 220 to hold the various portions of the cuff 224 in place on the frame 220. In the embodiment of FIGS. 8A and 8B, stitching 248 is made at two different axial regions along the frame 220. However, in other embodiments, more or less stitching 248 may be employed as needed to retain the cuff 224 on the frame 220, or any other suitable retention means may be used to hold the foam layer 242 and the fabric layer 244 in place on the frame 220, instead of the sleeve layer 246 and stitching 248. Furthermore, in other embodiments, only the foam layer 242 is utilized without the fabric layer 244, or only the fabric layer 244 is utilized without a foam layer 242, or a ring of any other suitable material can be used to form the annular cuff 224. The layer or layers of the annular cuff 224 will generally be made of one or more bio-compatible materials, and will generally be made of a material or materials that are softer or less rigid than the materials or alloys used in the stent frame 220.

Figure 9A:
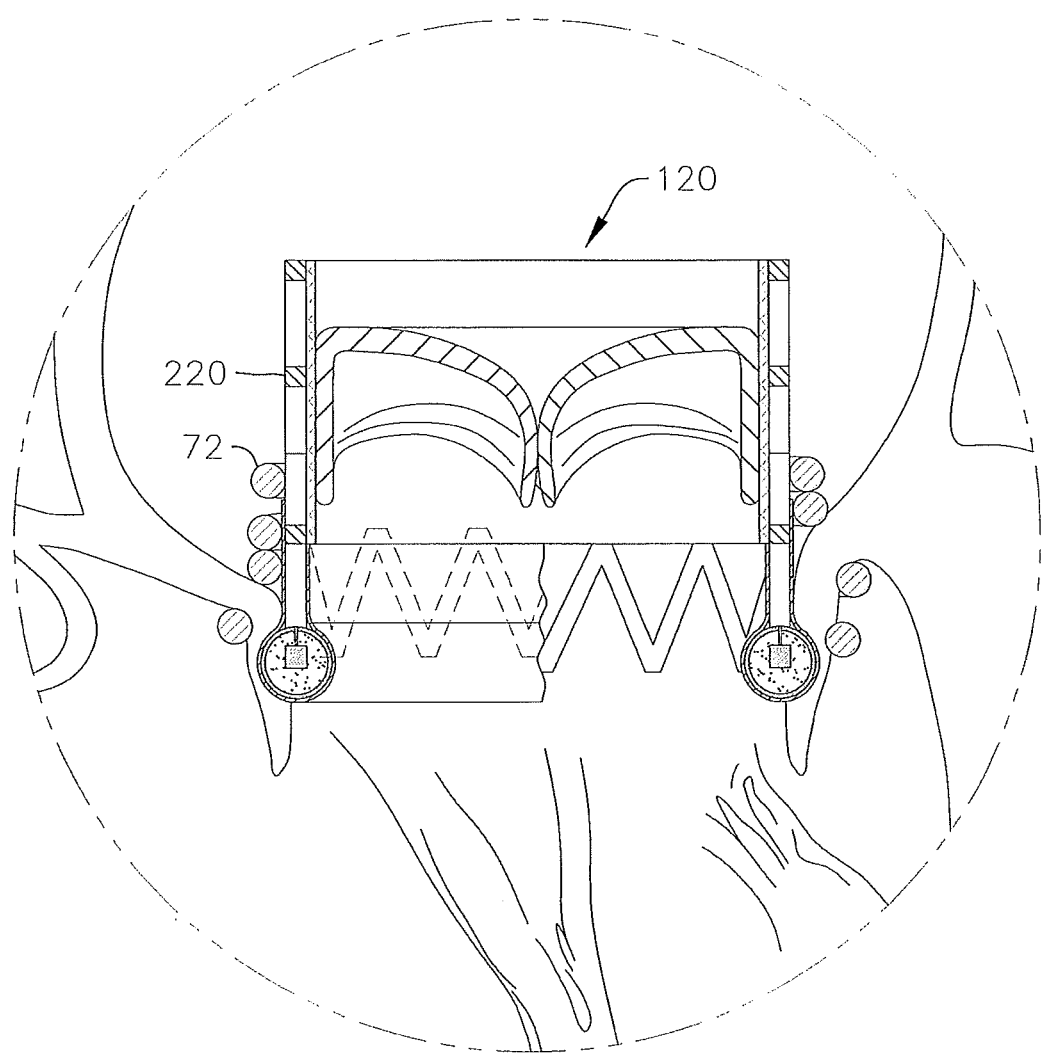

FIG. 9A shows an expanded valve prosthesis 120 anchored in a helical anchor 72 according to an embodiment of the invention. FIG. 9B schematically illustrates a tendency of the top and bottom ends of the valve prosthesis 120 to advantageously flare radially outward (e.g., in the direction of the arrows) upon deployment of the prosthesis 120 in a helical anchor 72, due to the frictional and resistive forces between the portions of the prosthesis 120 and the anchor 72 that contact one another. As discussed above with respect to the anchor 72 in FIGS. 3A to 3E, a core of the coil anchor according to embodiments of the invention is covered with a foam layer and/or a fabric layer, which each serve to promote ingrowth after implantation of the anchor in the mitral position. Furthermore, the foam or cloth cover of the anchor 72 can serve to prevent or reduce trauma to the tissue that surrounds and comes into contact with the anchor 72.

In addition, the foam layer and/or fabric layer further serve to create additional friction upon contact between the anchor 72 and the frame of valve prosthesis 120 anchored therein. In the case of metal-based anchoring or docking stations that do not further include a foam and/or fabric layer thereupon, the material or materials of the anchoring or docking station may be similar to or the same as the material or materials making up the stent frame of the valve prosthesis. In these instances, when the valve prosthesis is expanded in the coil anchor and the stent frame of the prosthesis begins to contact the coil anchor, there may be minimal or low frictional resistance between the stent frame and the coil anchor. Since the unbiased inner diameter of the coil anchor is generally smaller than the outer diameter of the expanded valve prosthesis, and due to the general wound structure of the helical coil, expansion of the valve prosthesis against the helical coil will urge at least the smallest diameter turns of the coil anchor to stretch radially outward and to partially unwind. This, in turn, can cause a slight dislodging or shifting of the anchor within the mitral valve annulus that may be undesirable and cause less effective functionality of the implanted valve prosthesis, or in a worst case, may lead to a weaker anchoring of the valve prosthesis in the coil anchor and potential embolization of the valve prosthesis out of the mitral valve annulus and into the left atrium or the left ventricle.

The foam and/or cloth or fabric covered coil anchor 72 according to embodiments of the invention serve to add friction between the coil anchor 72 and valve prosthesis 120 upon contact between the respective parts. Initially, when the valve prosthesis 120 is expanded in the coil anchor 72 during implantation of the replacement valve, the metal or metal alloy frame 220 of the valve 120 will come into contact with the foam 182 or fabric 184 layer of the coil anchor 72, and a circumferential frictional force between the contacting surfaces prevents the coil anchor 72 from sliding or unwinding under the radially outward forces applied by the expanding frame 220. Such frictional forces can be generated, for example, from the difference in materials between the outer surface of the cloth or foam covered coil 72 and the metal or alloy frame 220 of the valve prosthesis 120, from interference between the texturing of the cloth or foam covered coil 72 against the metal or alloy surface or various edges of the expandable stent frame 220 of the prosthesis 120, or from an interference or "catching" between the cloth or foam covered coil 72 with the edges, transitions or hinges, and/or stitchings on the outer surface of the frame 220 of the prosthesis 120. In other embodiments, other means or reasons for a circumferential friction or locking between the surfaces of the coil anchor 72 and the valve prosthesis 120 can be utilized or employed, in order to prevent or reduce circumferential migration or expansion of the helical coil 72 upon radially outward pressure applied from the expanding valve prosthesis 120.

According to embodiments of the invention, a helical coil 72 with a predefined opening size can more accurately be selected and implanted in a mitral valve annulus for holding or supporting a valve prosthesis therein. A surgeon or practitioner can more accurately select a coil size and shape together with a desired valve type and size, and the interaction between the pieces after implantation will be more predictable and robust. The valve prosthesis can be retained more securely in the coil anchor 72, since there will be a tighter hold or retention force between the anchor and the prosthesis, and since there will be less expansion, shifting, or migration of the anchor within the native mitral valve annulus upon expansion of the prosthesis therein.

Furthermore, the characteristics of the cloth or foam covered coil anchor 72 according to embodiments of the invention can also assist in easier implantation and positioning of the coil anchor 72 itself in the mitral valve annulus, prior to delivery of the valve prosthesis. First, due to the additional frictional forces contributing to helping later maintain the structural integrity and/or general size and shape of the coil anchor 72 against an expanded valve prosthesis, the core of the coil can be made to be thinner and/or more flexible, which makes the initial delivery of the coil anchor 72 through the coil guide catheter and into position in the mitral valve annulus easier. In addition, while a coil with a smaller diameter inner opening generally holds a valve prosthesis more securely, since undesired expansion of the coil anchor 72 by the valve prosthesis is prevented or reduced, the coil anchor 72 can also be made slightly larger than comparable coil anchors without a foam/cloth cover layer, and advancement of the anchor 72 around the native mitral valve leaflets and chordae tendineae during deployment of the anchor 72 can be more easily facilitated.

Referring now to FIG. 9B, another advantageous feature of the foam and/or cloth covered coil anchor is schematically illustrated. In FIG. 9B, only a portion of a valve prosthesis 120 that has been expanded in a coil anchor has been illustrated, with the coil anchor 72 removed for simplicity, in order to highlight the effect of the coil anchor on a valve prosthesis 120 implanted therein. As can be seen in FIG. 9B, the frame 220 of the valve prosthesis 120 has ends that have flared radially outwards. The frames 220 of the valve implants 120 used in accordance with embodiments of the invention generally have a constant expanded width or diameter along the length of the implant. As described above, a coil anchor will generally be selected to have an inner opening that has a diameter that is smaller than the expanded diameter of the valve prosthesis 120. Since the friction between the coil anchor 72 and the valve prosthesis 120 prevents or reduces uncoiling of the coil anchor, and therefore also prevents widening of the opening defined by the coil anchor, an interference fit is formed between the coil anchor and the portions of the valve prosthesis 120 that it comes into contact with. Generally, the valve prosthesis 120 will be centered or substantially centered on the coil anchor 72, where the coil anchor 72 directs an inward or resistive force against a central portion of the valve prosthesis 120, as illustrated by the arrow pointing towards the center of the prosthesis in FIG. 9B. The central portion of the valve prosthesis 120 will therefore be restricted from expanding to its fully expanded size. It should be noted that either the prosthetic valve size, the size of the coil anchor, or both, can be selected so as to account for this somewhat less-than-full expansion, to avoid compromising the hemodynamics through the prosthetic valve upon implantation. Meanwhile, the top and bottom ends of the valve prosthesis 120, which may not come into contact with the coil anchor 72, will continue to try to expand outwards towards their fully expanded size, as further illustrated by the arrows near the ends of the prosthesis in FIG. 9B, creating a flaring at the ends of the implant.

Figure 10A:
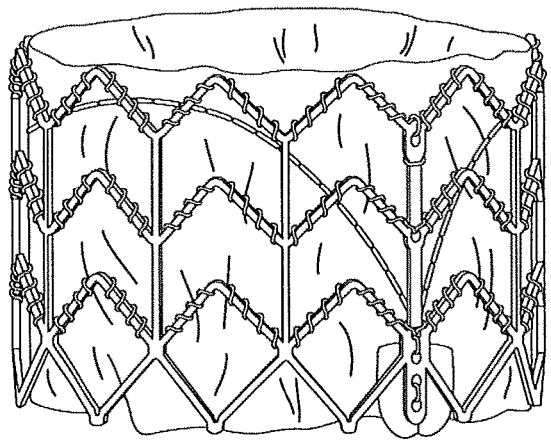
FIGS. 10A and 10B are respective images illustrating the flaring effect of a valve prosthesis according to an embodiment of the invention.
Figure 10B:
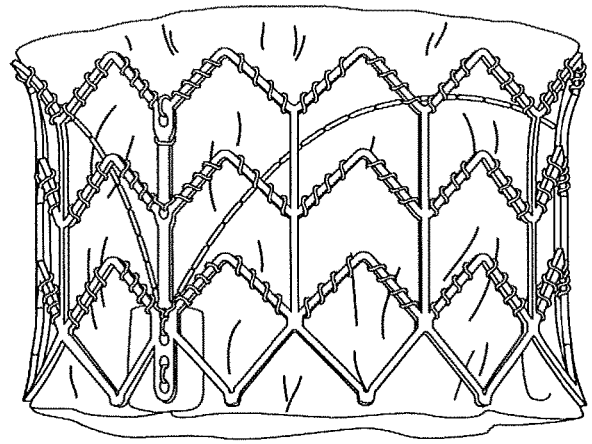

FIG. 10A shows a valve prosthesis according to an embodiment of the invention that has not been implanted in a foam or cloth covered coil anchor, while FIG. 10B shows the valve prosthesis after it has been expanded within a foam or cloth covered coil anchor and with the anchor removed, exhibiting the flaring or widening at the ends of the prosthesis as discussed above.

The flaring exhibited in the valve prosthesis 120 provides a number of benefits. The locking dynamic created between the contacting surfaces of the coil anchor and the valve prosthesis, coupled with the flared frame geometry of the prosthesis 120, combine to increase retention of the anchor within the coil anchor and the mitral valve annulus. The flaring and widening of the ends of the valve prosthesis 120 add a dimension to the ends of the prosthesis that serve to create an additional abutment and obstacle against dislodging of the valve from the coil anchor and potential embolization of the valve under elevated pressures within the heart. In preliminary tests, while pulsatile pressures up to 70 mmHG and static pressures up to 150 mmHg applied against a valve prosthesis anchored in an uncovered metal coil in separate tests did not dislodge the prosthetic valve from the coil anchor, the prosthetic valve did dislodge from the uncovered anchor at higher static pressures, for example, pressures above 290 mmHg. Meanwhile, prosthetic valves that were anchored in a covered coil anchor according to embodiments of the invention were successfully retained in all of the above tests. Therefore, a prosthetic valve can be more effectively retained in a foam and/or cloth covered coil anchor. In addition, flaring of the sub-annular portion of the prosthetic valve (i.e., the portion of the valve located in the left ventricle) will also more securely pinch or hold the native leaflets of the mitral valve against sub-annular portions of the coil anchor, further improving retention of the implant.

Flaring of the ends of the valve prosthesis 120 will increase contact between the prosthesis 120 and the surrounding heart tissue, such as the native mitral valve leaflets and the chordae tendineae. This could potentially lead to damage of the surrounding tissue by sharp edges or corners on the frame 220 of the valve. Referring back to the valve prosthesis illustrated in FIGS. 8A-9B, the annular cuff 224 is therefore added to the sub-annular end of the valve prosthesis 120 to protect the surrounding tissue of the heart from the flared ends of the frame 220 which could potentially dig into, cut, or otherwise damage the tissue.

Figure 11A:
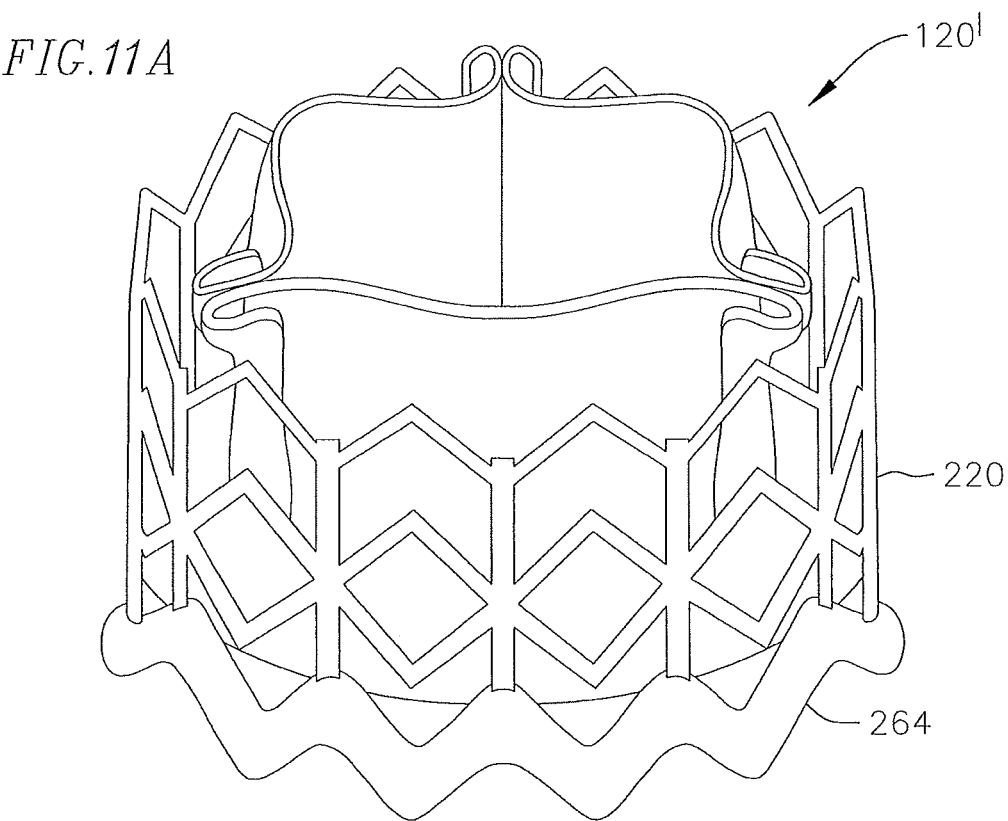
FIGS. 11A and 11B are schematic images showing a cuff or protective layer added to a valve prosthesis according to other embodiments of the invention.
Figure 11B:
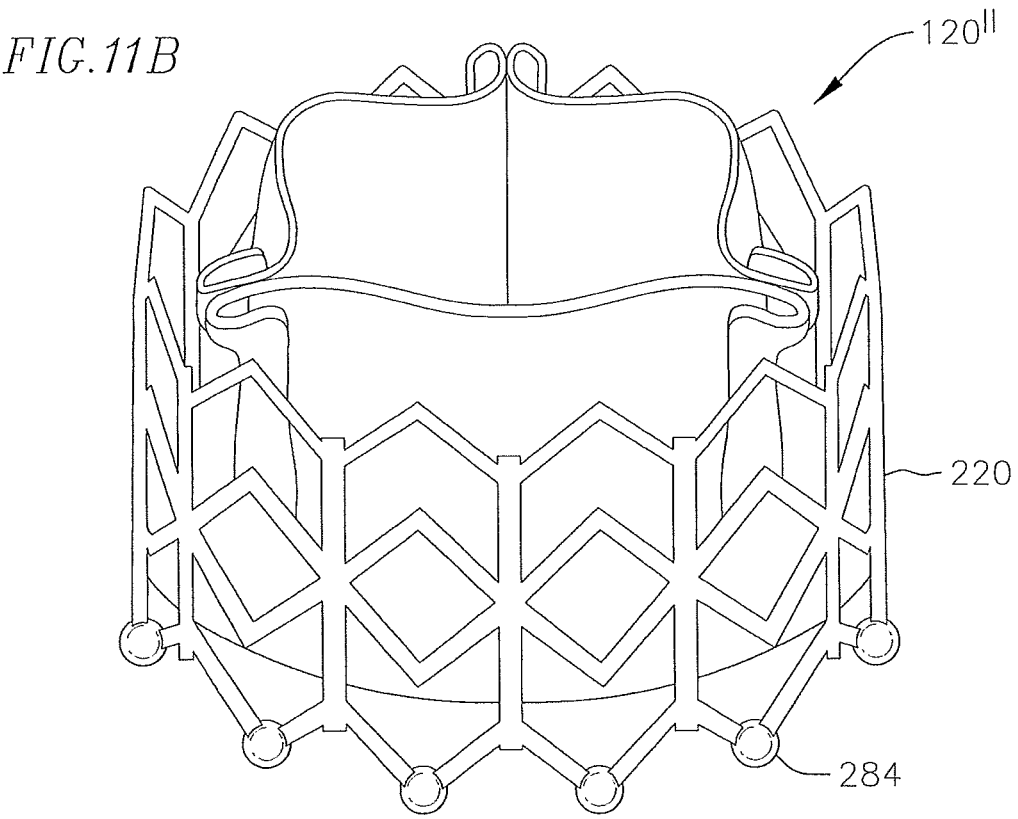

As seen in the previously described embodiments, the annular cuff 224 is realized as a continuous annular ring covering at least the corners on one end of the stent frame 220 of the valve prosthesis. Meanwhile, FIGS. 11A and 11B illustrate two alternative protective cuff arrangements. In FIG. 11A, an alternative cuff layer 264 traces along the bottom (i.e., the sub-annular) edge of the stent frame 220 of the valve prosthesis 120, in order to provide increased protection of the surrounding tissue from the entire bottom edge contour of the stent frame 220. In FIG. 11B, another alternative protective layer 284 is realized by spherical or ball-shaped protectors attached to the lowermost corners of the stent frame 220. The protective layer 284 in FIG. 11B, or other similar low profile arrangements, may be desirable in some applications since, for example, a stent frame having a lower profile protective layer will be easier to collapse and deliver through a catheter or delivery sheath. In addition, while various different protective layers are illustrated as being added only to a sub-annular end of the valve prosthesis 120 in the described embodiments, it will also be understood that similar cuff layers or other protective layers can be added to other portions of the valve prosthesis 120 in order to prevent or reduce trauma to other portions of the surrounding tissue caused by the expansion and/or flaring of the stent frame 220.

Figure 12:
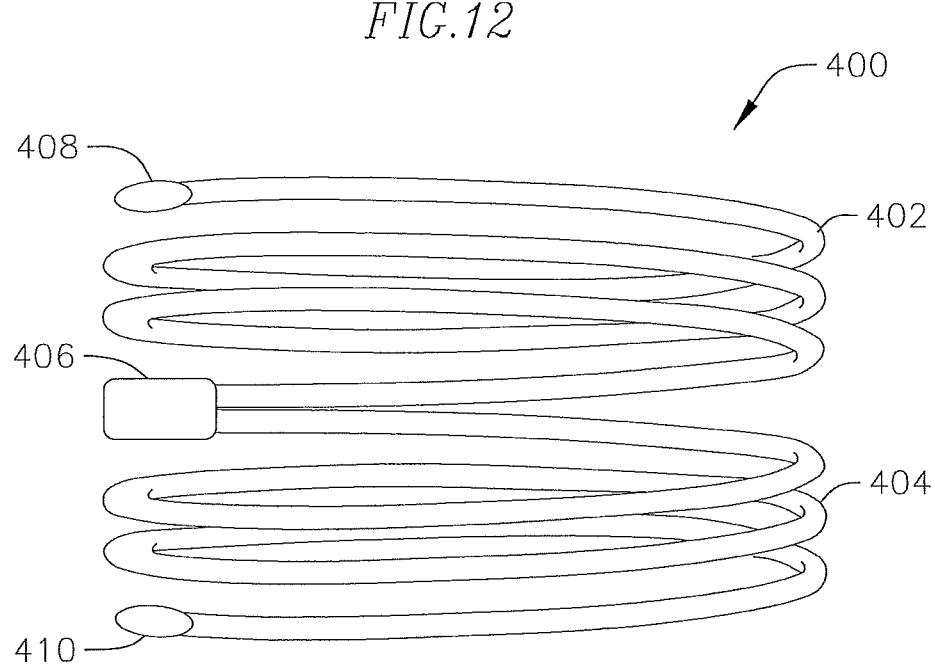
FIG. 12 shows a perspective view of a helical coil anchor according to another embodiment of the invention.

The coil anchor 72 described in the previous embodiments is made up of or includes one helical coil. FIG. 12 shows a perspective view of a coil anchor according to another embodiment of the present invention. In FIG. 12, the coil anchor 400 includes a first coil 402 that is wound in a first circumferential direction, and a second coil 404 that is wound in a second circumferential direction opposite to the first circumferential direction. Therefore, the first and second coils 402, 404 can be aligned next to each other along a longitudinal axis of the coils, and at least a length of each of the coils 402, 404 nearest to one another can be aligned or pushed up against one another. In this configuration, the adjacent ends of the coils 402, 404 are joined together at a joint 406, which in one example is a crimp joint. In another example, the adjacent ends of the coils 402, 404 are bonded or welded together, or are held together in one of various other bio-compatible means, and with or without other bio-compatible materials, that integrates the coils 402, 404 into one single anchor or docking station. The coils 402, 404 extend and wind from the joint 406 in opposite directions, and the first or upper coil 402 terminates in an upper distal end 408, while the second or lower coil 404 terminates in a lower distal end 410. The upper coil anchor 402 (or atrial anchor) is so named because the upper coil 402 will be positioned in the left atrium, above the mitral valve annulus, once deployed. Similarly, the lower coil anchor 404 (or ventricular anchor) is so named because most of the lower coil 404 will be advanced or fed through the mitral valve at a commissure and will be positioned sub-annularly, below the mitral valve annulus, in the left ventricle once deployed. In some embodiments, the coil anchor 400 can have a cover layer or layers similar to the cover layers discussed above with respect to the coil anchor 72. In these embodiments, a core of the coil anchor 400 can be covered, for example, by a fabric layer, a foam layer, or another bio-compatible material, or by a combination of such layers.

Figure 13A:
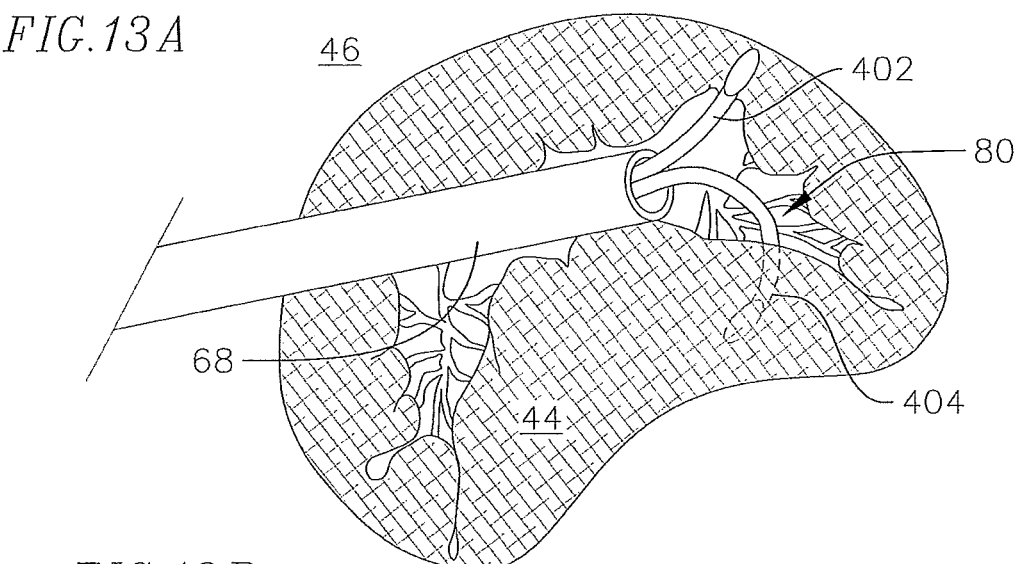
FIGS. 13A and 13B respectively show the helical coil anchor of FIG. 12 being deployed at a mitral position, and the helical coil anchor of FIG. 12 in its final deployed position.

The coil anchor 400 can initially be deployed similarly to the coil anchor 72 in previously described embodiments. As seen in FIG. 13A, a coil guide catheter 68 is positioned in the left atrium 46, near a mitral valve commissure 80. The coil anchor 400 is advanced and begins extending out of the distal opening of the coil guide catheter 68, and the distal end 410 of the lower coil 404 is directed through the valve at the commissure 80 to a sub-annular position in the left ventricle. The coil anchor 400 can be advanced via push-out force or load, can be pulled out, the sheath can be withdrawn, or the anchor 400 can be delivered from the coil guide catheter 68 using one of various other known deployment methods. The lower coil 404 is thereafter positioned similarly to the coil anchor 72 in previous embodiments. However, during deployment of the lower coil 404, the upper coil 402 simultaneously advances out of the distal end of the coil guide catheter 68, and begins unwinding in an opposite direction, and upwards into the left atrium. Due to the opposite winding directions of the upper and lower coils 402, 404, the central axes of the two coils can remain substantially aligned during and after deployment of the anchor 400. Furthermore, due to the opposite winding directions, the upper and lower coils 402, 404 will naturally curl or wind in opposite directions when they exit from the coil guide catheter 68, and will advance away from one another along a central axis of the coil anchor 400 during deployment. In this manner, once the lower coil 404 is directed through the valve at the commissure 80, since the upper coil 402 will deploy upwards rather than following the direction of advancement of the lower coil 404, the upper coil 402 will naturally move away from the commissure 80, and will not inadvertently be guided through the valve at the commissure 80.

Figure 13B:
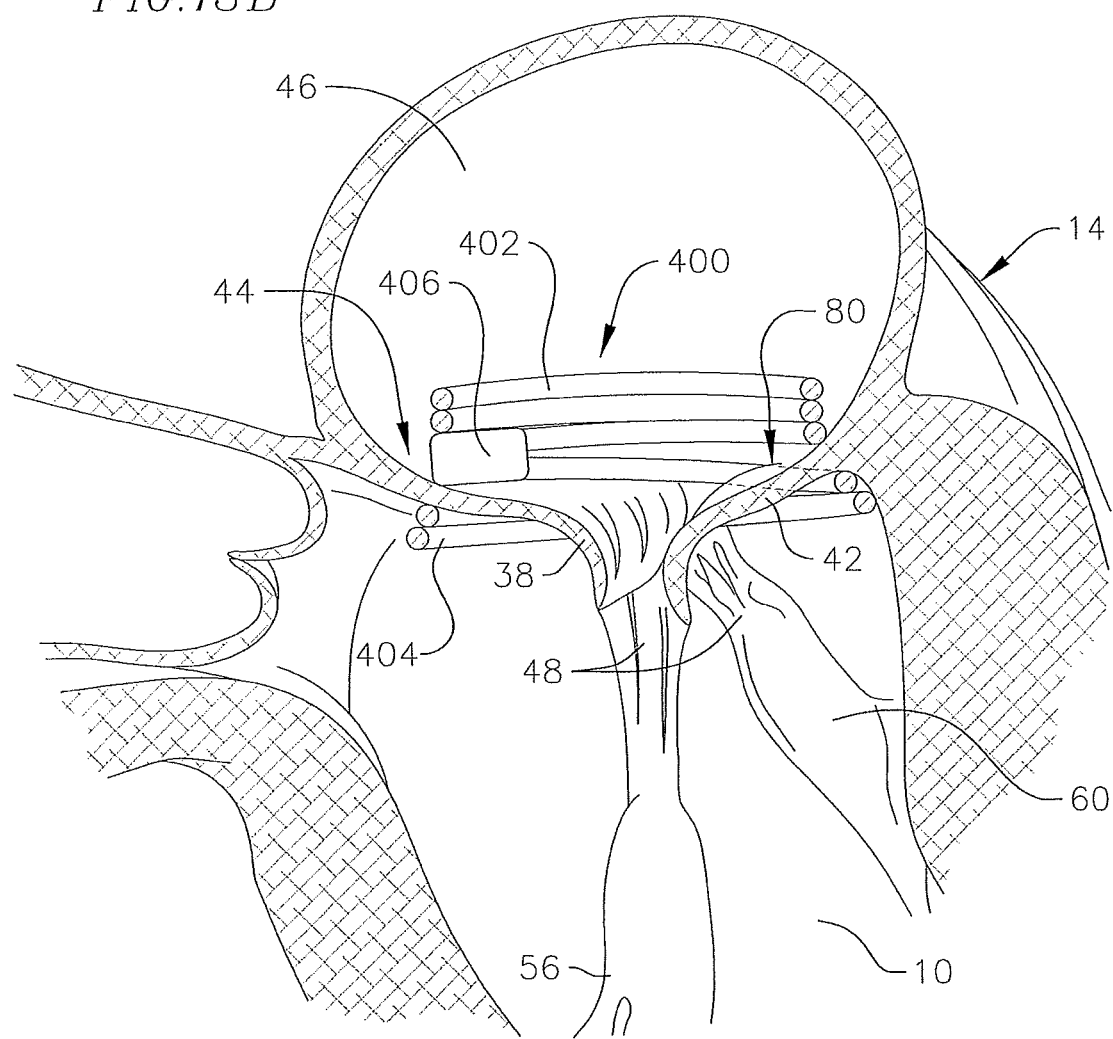

The coil anchor 400 is advanced until the joint 406 exits the distal end of the coil guide catheter 68. Additional adjustments of the anchor to a final desired position may further be made by the practitioner after the coil anchor 400 has exited the catheter 68, as needed. As can be seen in FIG. 13B, the coil anchor 400 is deployed to be arranged similarly to the coil anchor 72 in previous embodiments. In addition, since the upper and lower coils 402, 404 are deployed and positioned at the same time, and since the coil guide catheter can remain in substantially a same position throughout deployment of the coil anchor 400, a latter step of rotating the coil guide catheter 68 in order to release an upper portion of the anchor into the left atrium is no longer necessary, simplifying the anchor implanting procedure.

In some embodiments, the upper and lower coils 402, 404 of the coil anchor 400 can be staggered, where the lower coil 404 is slightly longer than the upper coil 402. In this manner, the distal end 410 of the lower coil 404 is configured to exit the distal end of the coil guide catheter 68 first, for easier positioning of the distal end 410 through the valve at the commissure 80. After the distal end 410 of the lower coil 404 is positioned through the valve at the commissure 80, the anchor 400 can be fully advanced and positioned without adjustment, or with only minor adjustments, to the position of the coil guide catheter 68. In other embodiments, the upper and lower coils 402, 404 are substantially the same length, or the upper coil 402 can be longer than the lower coil 404. The relative lengths of the two coils of the coil anchor 400 can be adjusted based on the needs of the patient and the preferences of the practitioner, among other factors.

As has been seen in previous embodiments, different coil anchors can be deployed at the mitral position in different manners. In each embodiment, it is important that the leading end, or distal end, of the sub-annular coil (i.e., the portion of the coil anchor that advances through the mitral valve into the left ventricle) is directed completely around the native leaflets of the mitral valve and around the chordae tendineae, in order for the anchor to remain closely positioned to the mitral valve annulus. For example, if the distal end of the coil does not go completely around the chordae tendineae, and is instead advanced between two chordae, the coil may become entangled in the chordae, and/or the sub-annular portion of the coil anchor may be held under tissue where the two chordae meet, and thus be deflected farther away from the valve annulus than desired. Such a scenario can have negative effects, such as damage to the coil anchor and/or the chordae tendineae or the native mitral valve leaflets, or unstable anchoring or poor positioning of a valve prosthesis that is held in the coil anchor.

Figure 14:
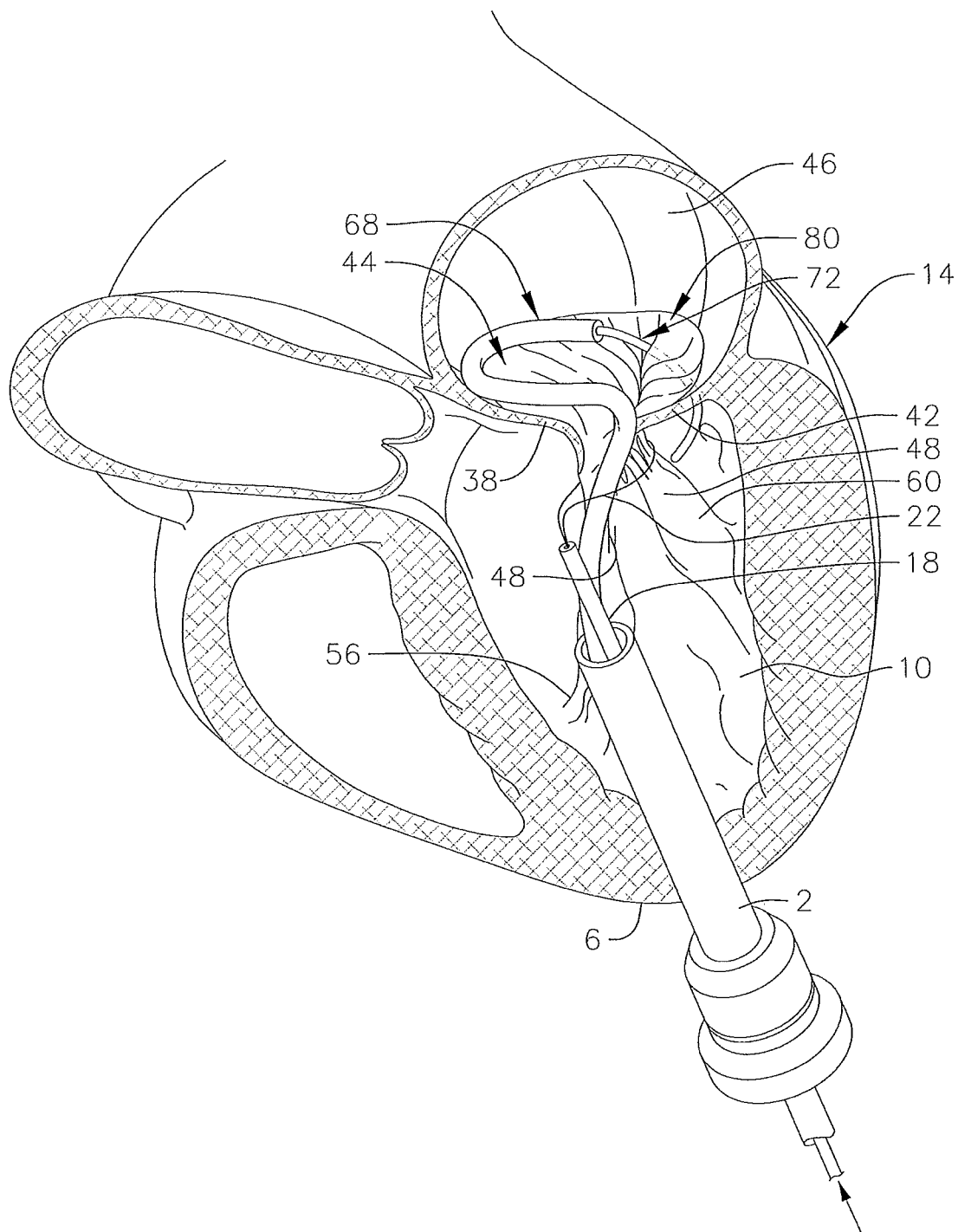
FIG. 14 shows a modified deployment system according to another embodiment of the invention.

FIG. 14 shows a coil anchor deployment system according to an embodiment of the invention. In some embodiments, the deployment system has an arrangement similar to that of previously described embodiments, with an introducer 2, a delivery catheter 64, and a steering catheter or coil guide catheter 68 through which a helical anchor 72 is delivered. In the embodiment illustrated in FIG. 14, the introducer 2 is positioned through the left ventricle 10, but in other embodiments, the introducer 2 and/or other delivery catheters can be positioned through the atrial septum, or any other access site that is suitable for delivery of a helical anchor.

In addition to the catheters associated with the delivery of the helical anchor, a separate catheter 18 can be included in the deployment system, and can also be fed and advanced through the introducer 2 or other sheath or cannula in the deployment system. At a distal end of the catheter 18, a temporary ring or loop 22 is provided, which is used to corral, bundle, "lasso," or otherwise draw the chordae tendineae 48 together prior to deployment of the helical anchor 72. The chordae tendineae 48 then occupy a smaller cross-sectional area in the left ventricle 10, which facilitates easier later deployment of the distal tip of the helical anchor 72 around the chordae, and placement of the helical anchor 72 in the desired or optimal position without any chordal entanglement.

The temporary ring or loop 22 can be, for example, a suture or a guide wire, or any other suitable thread or wire. In some embodiments, the loop 22 is led or guided around the chordae tendineae 48 with for example, a grasping tool or one or more other tools introduced through the introducer 2 or through another delivery sheath or cannula. In other embodiments, the loop 22 is advanced through one or more segmented guiding catheters around the chordae tendineae 48. In these embodiments, the loop 22 is closed, for example, by utilizing a clamping tool or a grasping tool, via tying, or by one of various other attachment methods, and then the segments of the guiding catheter or catheters are retracted, leaving the loop 22 in its final position around the chordae. In yet other embodiments, the loop 22, like the helical anchor 72, is pre-formed to have a curvature, such that the loop 22 surrounds the chordae tendineae as it is deployed. In some embodiments, after the loop 22 has been closed, an opening defined by the loop 22 can further be tightened or narrowed, to further bundle or corral the chordae tendineae 48 closer together. Meanwhile, while FIG. 14 shows the catheter 18 and loop 22 deployed together with the delivery catheter 64 and the coil guide catheter 68, in other embodiments, any combination of catheters can be present when the loop 22 is deployed around the chordae tendineae 48. For example, in previously described embodiments, the delivery catheter 64 is retracted before the coil anchor 72 is deployed, and a similar process can be followed here. Furthermore, in embodiments where the introducer 2 is positioned in an apical access site, the loop 22 can also loop around the introducer and/or one or more of the delivery or coil guide catheters. If, instead, a transseptal procedure is performed, a distal end of the loop catheter 18 can instead be advanced through the mitral valve from the left atrium into the left ventricle, and the loop 22 can be deployed around the chordae tendineae 48, without also bundling or corralling any additional delivery catheters or tubes therein.

After the loop 22 is deployed around the chordae tendineae 48 and bundles or otherwise draws the chordae together, and after the helical coil anchor 72 is deployed fully around the chordae and is satisfactorily docked in the mitral position, the loop 22 is removed. This can be accomplished, for example, by a release of the grasping tool if one is utilized, and/or by untying or cutting the suture, thread, or guide wire used for the loop 22, and then removing the loop together with the other tools and catheters in the deployment system from the access site.

In embodiments where a loop as described above is utilized in a coil anchor deployment system, issues arising from a coil anchor being entangled in the chordae tendineae during deployment, or from a coil anchor being stuck between two or more chordae and being positioned incorrectly, can be mitigated or prevented. In this manner, the anchor can be more securely positioned, and a valve prosthesis can also be more securely deployed and implanted therein.

Various other modifications or alternative configurations can be made to the helical anchors, valve prostheses, and/or deployment systems according to the above described embodiments of the invention. For example, in the illustrated embodiments, the coils of the helical anchors are tightly wound near the mitral valve annulus. In other embodiments, some of the coils of the anchor may be widened or flared outwards to make contact with, for example, the atrial wall of the left atrium. Furthermore, the number of coils both above and below the valve annulus can be varied, based on for example, properties of the native mitral valve and/or desired positioning of the valve prosthesis. In embodiments where upper and lower coils are joined together to form the helical anchor, the two coils can be prepared, modified, and/or selected separately based on a patient's anatomy or various other factors. In addition, other modifications to the deployment system can be employed in order to more efficiently or effectively bundle the chordae tendineae during deployment and positioning of the helical anchor. Various other coil shapes, lengths, and arrangements and modifications can also be made based on a wide range of considerations.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

In view of the many possible embodiments to which the principles of the disclosure may be applied, it should be recognized that the illustrated embodiments are only preferred examples and should not be taken as limiting the scope of the disclosure. Rather, the scope of the disclosure is defined by the following claims.

What is claimed is:

1. A system for replacing a native valve of a heart comprising:
an anchor having a first end, a second end, a coiled region, a central axis extending through a middle of the coiled region, and defining an inner space coaxial with the central axis, the anchor comprising:
a core comprising a bio-compatible material; and
a cover layer around the core;
wherein the anchor is adjustable from the first position to a second position and from the second position back to the first position, and wherein, in the second position, at least a portion of the coiled region is straightened such that the anchor can be delivered through a catheter to the native valve; and
wherein the anchor is implantable with at least one turn of the coiled region positioned radially around native leaflets and/or chordae tendieae of the native valve; and
a prosthetic valve for docking within the anchor, the prosthetic valve comprising an expandable frame and a plurality of leaflets for controlling blood flow through the prosthetic valve, wherein the frame is expandable from a collapsed first configuration in which the frame has a first outer diameter for delivery of the prosthetic valve through a catheter to an expanded second configuration in which the frame has a second outer diameter greater than the first outer diameter;
wherein the frame of the prosthetic valve has a first frame end and a second frame end, and the prosthetic valve further comprises a protective annular ring that includes two different materials and surrounds a bottom edge of the second frame end.

2. The system of claim 1, wherein the cover layer comprises a fabric layer.

3. The system of claim 1, wherein the cover layer comprises a fabric layer surrounding a foam layer.

4. The system of claim 1, wherein when the prosthetic valve is held in the inner space of the anchor, at least a portion of the frame within the inner space is restricted from fully expanding due to forces from the anchor.

5. The system of claim 4, wherein the system is configured such that, when the prosthetic valve is held in the inner space of the anchor, a frictional force is generated to restrict circumferential motion between the anchor and the prosthetic valve, such that circumferential unwinding of the anchor and radial expansion of the inner space of the anchor is restricted.

6. The system of claim 4, wherein another portion of the frame is configured to expand radially outwardly to a diameter that is greater than a diameter of the portion of the frame within the inner space that is restricted from fully expanding due to forces from the anchor.

7. The system of claim 1, wherein the protective annular ring comprises at least one of a foam layer or a fabric layer.

8. The system of claim 1, wherein when the anchor and the prosthetic valve are unbiased, a smallest inner diameter of the inner space defined by the anchor is smaller than the second outer diameter of the prosthetic valve.

9. A system for treating a native valve of a heart comprising:
an anchor having a first end, a second end, and a coiled region defining an inner space, wherein the anchor is adjustable between a first configuration to a second configuration, wherein, in the second configuration, the coiled region is straightened enough to allow the anchor to be elongated and delivered through a catheter to the native valve, and wherein the anchor is implantable at the native valve with at least one turn of the coiled region is positioned around native leavlets and/or chordae tendineae of the native valve; and a prosthetic valve for docking within the anchor, the prosthetic valve comprising an expandable frame and a plurality of leaflets for controlling blood flow through the prosthetic valve, wherein the frame is expandable from a collapsed first configuration in which the frame has a first outer diameter for delivery of the prosthetic valve through a catheter to an expanded second configuration in which the frame has a second outer diameter greater than the first outer diameter;

wherein the frame of the prosthetic valve includes bottom end corners, and the prosthetic valve further comprises a protective cuff that comprises two layers and surrounds the bottom end corners of the frame.

10. The system of claim 9, wherein the anchor includes a core and a cover over the core, and wherein the cover comprises a fabric layer.

11. The system of claim 9, wherein the anchor includes a core and a cover over the core, and wherein the cover comprises a fabric layer surrounding a foam layer.

12. The system of claim 9, wherein the anchor is configured to generate a frictional force such that circumferential unwinding of the anchor is restricted.

13. The system of claim 9, wherein the protective cuff comprises an annular ring extending around an outflow end of the frame.

14. The system of claim 9, wherein the protective cuff comprises at least one of a fabric layer or a foam layer.

15. The system of claim 9, wherein the protective cuff comprises a first fabric layer surrounding a second layer of a different material from the first fabric layer.

16. A system for implanting at a native valve comprising:
an anchor for docking a prosthetic valve at a native valve of a heart and having a first end, a second end, and a coiled region defining an inner space, the anchor comprising:
  a core comprising a bio-compatible metal or metal alloy; and
  a cover around the core, the cover layer comprising a bio-compatible material that is less rigid than the metal or metal alloy of the core;
wherein the anchor is adjustable from a first coiled configuration to a second elongated configuration wherein the coiled region is straightened such that the anchor can be passed through a catheter in the second straightened configuration to the native valve; and
wherein the anchor is implantable at the native valve with at least a portion on one side of the native valve in an atrium of the heart and at least a portion including multiple turns on an opposite side of the native valve in a ventricle of the heart surrounding native leaflets and/or chordae tendineae of the native valve; and
a prosthetic valve comprising an expandable frame housing a plurality of leaflets for controlling blood flow therethrough, and wherein the frame is expandable from a collapsed first configuration wherein the frame has a first outer diameter for delivery of the prosthetic valve through a catheter to an expanded second configuration wherein the frame has a second outer diameter greater than the first outer diameter;
wherein, when the anchor and the prosthetic valve are unbiased, a smallest inner diameter of the inner space defined by the coil anchor is smaller than the second outer diameter of the prosthetic; wherein the prosthetic valve further comprises a protective annular ring comprising two layers, the protective annular ring covering a bottom outflow edge of the frame.

17. The system of claim 16, wherein, when the prosthetic valve is held in the inner space of the anchor, a first portion of the frame is restricted from expanding to the second outer diameter by forces from the anchor.

18. The system of claim 17, wherein the system is configured such that, when the prosthetic valve is held in the inner space of the anchor, a frictional force is generated to restrict circumferential motion between the anchor and the prosthetic valve, such that circumferential unwinding of the anchor and radial expansion of the inner space of the anchor is restricted.

19. The system of claim 17, wherein, when the prosthetic valve is held in the inner space of the anchor, a second portion of the frame is configured to expand radially outwardly to a diameter that is greater than a diameter to which the first portion of the frame expands.

* * * * *